US009637551B2

(12) United States Patent
Bishop et al.

(10) Patent No.: US 9,637,551 B2
(45) Date of Patent: May 2, 2017

(54) MULTI-COMPONENT INHIBITORS OF NUCLEIC ACID POLYMERASES

(75) Inventors: John D. Bishop, Carlsbad, CA (US); Jun E. Lee, San Diego, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 138 days.

(21) Appl. No.: 12/636,655

(22) Filed: Dec. 11, 2009

(65) Prior Publication Data
US 2010/0209975 A1 Aug. 19, 2010

Related U.S. Application Data

(63) Continuation of application No. 11/341,870, filed on Jan. 30, 2006, now abandoned, which is a continuation-in-part of application No. 11/044,620, filed on Jan. 28, 2005.

(51) Int. Cl.
C12N 9/12 (2006.01)
C07K 16/40 (2006.01)
C12Q 1/68 (2006.01)

(52) U.S. Cl.
CPC ............ *C07K 16/40* (2013.01); *C12Q 1/6848* (2013.01)

(58) Field of Classification Search
None
See application file for complete search history.

(56) References Cited

U.S. PATENT DOCUMENTS

| | | | |
|---|---|---|---|
| 4,889,818 A | 12/1989 | Gelfand et al. | |
| 4,965,188 A | 10/1990 | Mullis et al. | |
| 5,047,342 A | 9/1991 | Chatterjee | |
| 5,079,352 A | 1/1992 | Gelfand et al. | |
| 5,180,810 A | 1/1993 | Gomi et al. | |
| 5,223,391 A | 6/1993 | Coen et al. | |
| 5,244,797 A | 9/1993 | Kotewicz et al. | |
| 5,270,179 A | 12/1993 | Chatterjee | |
| 5,338,671 A | 8/1994 | Scalice et al. | |
| 5,374,553 A | 12/1994 | Gelfand et al. | |
| 5,436,149 A | 7/1995 | Barnes | |
| 5,475,096 A | 12/1995 | Gold et al. | |
| 5,587,287 A * | 12/1996 | Scalice et al. | 435/6.18 |
| 5,614,365 A | 3/1997 | Tabor et al. | |
| 6,140,086 A * | 10/2000 | Fox et al. | 435/91.41 |
| 6,830,902 B1 | 12/2004 | Astatke et al. | |
| 7,045,319 B2 | 5/2006 | Hanna | |
| 2002/0037834 A1 | 3/2002 | Astatke et al. | |
| 2007/0020622 A1 | 1/2007 | Lee et al. | |
| 2010/0068767 A1 | 3/2010 | Bishop et al. | |
| 2010/0209975 A1 | 8/2010 | Bishop et al. | |

FOREIGN PATENT DOCUMENTS

| | | |
|---|---|---|
| EP | 0367890 | 5/1990 |
| EP | 0592035 | 1/1996 |
| GB | 2230011 | 10/1990 |
| WO | 92/06188 A2 | 4/1992 |
| WO | 92/06200 A1 | 4/1992 |
| WO | 96/10640 A1 | 4/1996 |
| WO | 97/09451 A1 | 3/1997 |
| WO | 98/47912 A1 | 10/1998 |
| WO | 02/095054 | 11/2002 |
| WO | 03/025132 | 4/2003 |
| WO | 2006/081462 | 8/2006 |

OTHER PUBLICATIONS

See Ngo et al. in The Protein Folding Problem and Tertiary Structure Prediction, 1994, Merz et al. (ed.), Birkhauser, Boston, MA, pp. 433 and 492-495.*
Choi et al., Biotechnol. Appl. Biochem, vol. 30, pp. 19-25. 1999.*
Astatke, Mekbib et al., "How *E. coli* DNA Polymerase I (Klenow fragment) distinguishes between Deoxy-and Dideoxynucleotides", *The Journal of Molecular Biology,*, vol. 278, Academic Press Ltd.,, Apr. 1998, pp. 147-165.
Astatke, Mekbib et al., "U.S. Appl. No. 09/570,526", filed May 12, 2000, 67 pages.
Barnes, , "The Fidelity of Taq Polymerase Catalyzing PCR is Improved by an N-Terminal Deletion", *Gene*, vol. 112, No. 1, Mar. 1, 1992, 29-35.
Duque, Hernando et al., "Epitope Mapping of Monoclonal Antibodies Raised to Recombinant Mengo 3D Polymerase", *Virus Genes,*, 1996, vol. 13, No. 2, 159-168.
EP06719730.1, , *European Search Report*, Mailed Sep. 30, 2009, 3 pages.
Fagan, Peter et al., "Identification and Characterization of a Novel Secreted Immunoglobulin Binding Protein from Group A *Streptococcus*", *Infection and Immunity,*, vol. 69, No. 8 2001, 4851-4857.
Genbank, "thermostable DNA polymerase [Thermus filiformis]", *GenBank: AAC46079.1*, Downloaded at URL: http://www.ncbi.nlm.nih.gov/protein/AAC46079 on Jul. 17, 2012, Feb. 3, 1998, 2 pages.
Genbank, "Thermus filiformis thermostable DNA polymerase (pol) gene, complete cds", *GenBank: AF030320.1*, Downloaded at URL: http://www.ncbi.nlm.nih.gov/nuccore/AF030320 on Jul. 17. 2012, Feb. 4, 1998, 2 pages.
Gerard, et al., "cDNA Synthesis by Moloney Murine Leukemia Virus RNase H-Minus Reverse Transcriptase Possessing Full DNA Polymerase Activity", *Focus*, vol. 14, No. 3,, 1992, 91-93.
Jung, Seung E. et al., "Cloning and Analysis of the DNA Polymerase-encoding Gene from Thermus Filiformis", vol. 7, No. 6, *Molecules and Cells,*, 1997, 769-776.
Kotewicz, et al., "Isolation of cloned Moloney murine leukemia virus reverse transcriptase lacking ribonuclease H activity", *Nucleic Acids Research*, vol. 16, No. 1, Jan. 11, 1988, 265-277.
Lawyer, Frances C. et al., "High-level Expression, Purification, and Enzymatic characterization of Full-length Thermus aquaticus DNA polymerase and a Truncated Form Deficient in 5' to 3' Exonuclease activity", *PCR Methods and Applications,*, vol. 2, No. 4, Cold Spring Harbor Laboratory Press May 1993, 275-287.

(Continued)

*Primary Examiner* — Richard Hutson

(57) ABSTRACT

The present invention provides multi-component inhibitors of nucleic acid polymerases, methods of making, and methods of using same. One component of the multi-component inhibitor is a molecule that binds to a polymerase (i.e., a polymerase-binding molecule (PBM)), but does not thereby substantially inhibit its polymerase activity. Another component is a molecule or complex of molecules that binds to a PBM (i.e., a PBM-binding molecule). The combination of the PBM and PBM-binding molecule/complex substantially inhibits polymerase activity.

11 Claims, 14 Drawing Sheets

(56) References Cited

OTHER PUBLICATIONS

Lee, Jun et al., "U.S. Appl. No. 60/647,408", filed Jan. 28, 2005, 98 Pages.
Ngo, J., et al., "Computational Complexity, Protein Structure Prediction, and the Levinthal Paradox", in *The Protein Folding Problem and Tertiary Structure Prediction,*, Mertz et al., (editors), Birkhauser 1994, 433, 492-495.
PCT/US2006/003006, *International Search Report and Written Opinion*, Mailed Jul. 2, 2008, 10 pages.
PCT/US2006/003006, *International Preliminary Report on Patentability*, Mailed Mar. 19, 2009, 8 pages.
Saiki, Randall K. et al., "Primer-Directed Enzymatic Amplification of DNA with a Thermostable DNA Polymerase", *Science*, Reports, vol. 239,, Jan. 29, 1988, 487-491.
Shandilya, H., et al., "Thermophilic bacterial DNA polymerases with reverse-transcriptase activity", *Extremophiles*, vol. 8, No. 3,, 2004, 243-251.
Stenberg, Lars et al., "Molecular characterization of protein Sir, a streptococcal cell surface protein that binds both immunoglobulin A and immunoglobulin G", *J. Biol. Chem,*, vol. 269,, 1994, 13458-13464.

\* cited by examiner

MULTI-COMPONENT INHIBITORS OF NUCLEIC ACID POLYMERASES

CROSS REFERENCE TO RELATED APPLICATIONS

This application is a continuation-in-part of U.S. application Ser. No. 11/044,620, filed Jan. 28, 2005, which is entirely incorporated by reference herein.

BACKGROUND OF THE INVENTION

Field of the Invention

This present invention relates to compositions and methods for inhibiting nucleic acid polymerases. These compositions and methods may be used for nucleic acid synthesis, amplification, sequencing and cloning.

Related Art

Nucleic acid polymerases ("polymerases") are enzymes that catalyze the synthesis of nucleic acid molecules that are complementary to a nucleic acid template. Template-directed nucleic acid synthesis is an important aspect of many molecular biology research and diagnostic techniques and assays. Such techniques and assays typically involve extension of a nucleic acid primer designed to hybridize to a specific region of the template.

The yield and homogeneity of primer extension products made by polymerases can be adversely affected by "mispriming," i.e., hybridization of primers to inappropriate regions of the template, or to non-template nucleic acids. Extension of misprimed nucleic acids can produce high background and obscure detection of properly primed primer extension products. In addition, diversion of nucleic acid synthesis reaction constituents to extend misprimed nucleic acids can reduce the yield of properly primed primer extension products, reducing the sensitivity of detection. The yield of primer extension products also can be adversely affected by template or primer degradation (e.g., by a nuclease activity of a polymerase). Mispriming and template or primer degradation can occur, e.g., when nucleic acid synthesis mixtures containing template, primers and polymerase are maintained at temperatures associated with manufacture, shipping, storage or bench top assembly of such mixtures.

BRIEF SUMMARY OF THE INVENTION

The invention relates to multi-component polymerase inhibitors that can enhance the yield and/or homogeneity of primer extension products made by polymerases. Multi-component inhibitors include at least two components. One component of a multi-component inhibitor is a molecule that binds to a polymerase (i.e., a polymerase-binding molecule (PBM)) but does not substantially inhibit its polymerase activity. Another component of a multi-component inhibitor is a molecule or complex that binds to a PBM (i.e., a PBM-binding molecule). The PBM and PBM-binding molecule/complex together substantially inhibit polymerase activity.

The present invention relates to compositions comprising a nucleic acid polymerase; a polymerase-binding molecule (PBM) that binds to the polymerase and does not substantially inhibit the polymerase activity of the polymerase, and a PBM-binding molecule/complex that binds to the PBM, such that binding of the PBM and PBM-binding/complex together substantially inhibits the polymerase activity of the polymerase. A PBM can be an antibody (PBA), e.g., a monoclonal antibody. A PBM-binding molecule/complex can include an antibody, protein G, protein A, a derivatized antibody, a derivatized protein G, a derivatized protein A, IgG and/or a derivatized protein G, sir22, sib A. A PBM-binding molecule or complex can include a detectable label (e.g., rhodamine, biotin, fluorescein, horseradish peroxidase, alkaline phosphatase or AlexaFluor488), protein (e.g., horseradish peroxidase, alkaline phosphatase or albumin), or polymer (e.g., a polyethylene glycol, a polyoxyethylene, a polyoxypropylene or a polyoxyethylene/polyoxyethylene copolymer). A PBM-binding molecule/complex can include an antibody, for example, (a) IgA; (b) IgG; (c) IgM; (d) IgD; (e) IgE; (f) IgY; (g) a fragment of any of (a)-(f); (h) a derivative of any of (a)-(f); (i) a derivatized fragment of any of (a)-(h); and (j) a complex of any of (a)-(i). A PBM-binding molecule/complex can include a monoclonal antibody, polyclonal antibody, Fc antibody fragment, chimeric antibody or recombinant antibody, any of which can be derivatized with a detectable label (e.g., rhodamine, biotin, fluorescein, horseradish peroxidase, alkaline phosphatase or AlexaFluor488), protein (e.g., horseradish peroxidase, alkaline phosphatase or albumin) or polymer (e.g., polyethylene glycol, a polyoxyethylene, a polyoxypropylene or a polyoxyethylene/polyoxyethylene copolymer). A PBM-binding molecule/complex can include a goat anti-mouse IgG antibody coupled to horseradish peroxidase; a complex of a goat anti-mouse IgG antibody and protein G-horseradish peroxidase; protein G-AlexaFluor488; a goat anti-mouse IgG antibody; a complex of streptavidin and an antibody to mouse IgG coupled to biotin; and Protein G. A nucleic acid polymerase can be a DNA-dependent DNA polymerase or an RNA-dependent DNA polymerase, and can be thermolabile or thermostable. For example, the polymerase can be *Thermus aquaticus* (Taq), *Thermus filiformis* (Tfi), Tfi strain RT41A, *Pyrococcus furiosus* (Pfu), *Thermococcus zilligi* (Tzi), or a mutant of any of the above. A polymerase can recombinant.

The present invention also relates to compositions comprising a thermostable nucleic acid polymerase, a polymerase-binding antibody (PBA) that binds to the polymerase and does not substantially inhibit the polymerase activity of the polymerase, and a PBA-binding molecule/complex that binds to the PBA, such that binding of the PBA and PBA-binding molecule/complex together substantially inhibit the polymerase activity of the polymerase at a temperature less than about 40° C., and such that the binding of the PBA and PBA-binding molecule/complex together does not substantially inhibit the polymerase activity of the polymerase at a temperature greater than about 40° C. The nucleic acid polymerase can be a DNA-dependent DNA polymerase or an RNA-dependent DNA polymerase, and can be thermolabile or thermostable. For example, the polymerase can be *Thermus aquaticus* (Taq), *Thermus filiformis* (Tfi), Tfi strain RT41A, *Pyrococcus furiosus* (Pfu), *Thermococcus zilligi* (Tzi), or a mutant of any of the above. A polymerase can be recombinant.

The present invention also relates to methods of inhibiting the polymerase activity of a nucleic acid polymerase. Such methods involve contacting the polymerase with a polymerase binding molecule (PBM) and PBM-binding molecule/complex, where the binding of the PBM does not substantially inhibit the polymerase activity of the polymerase, and where the binding of the PBM and the PBM-binding molecule/complex together substantially inhibit the polymerase activity of the polymerase. Polymerase inhibition can be reversible (e.g., by heating to a temperature of at least about 40° C.). The PBM can be an antibody (PBA; e.g., a monoclonal antibody). The nucleic acid polymerase can be a DNA-dependent DNA polymerase or an RNA-dependent DNA polymerase. For example, the polymerase can be *Thermus aquaticus* (Taq), *Thermus filiformis* (Tfi), Tfi strain RT41A, *Pyrococcus furiosus* (Pfu), *Thermococcus zilligi* (Tzi), or a mutant of any of the above. A polymerase can be recombinant.

The present invention also relates to methods for synthesizing a nucleic acid molecule. Such methods involve contacting a template nucleic acid with a composition comprising a thermostable nucleic acid polymerase, one or more nucleoside and/or deoxynucleoside triphosphates, a polymerase binding molecule (PBM) that does not substantially inhibit the polymerase activity of the polymerase, and a PBM-binding molecule/complex under conditions where the PBM and the PBM-binding molecule/complex together substantially inhibit the polymerase activity of the polymerase; and bringing the resulting mixture to a temperature sufficient relieve polymerase inhibition. Polymerase inhibition can be relieved by heating to a temperature of at least about 40° C. The PBM can be an antibody (PBA; e.g., a monoclonal antibody). The nucleic acid polymerase can be a DNA-dependent DNA polymerase or an RNA-dependent DNA polymerase. For example, the polymerase can be *Thermus aquaticus* (Taq), *Thermus filiformis* (Tfi), Tfi strain RT41A, *Pyrococcus furiosus* (Pfu), *Thermococcus zilligi* (Tzi), or a mutant of any of the above. A polymerase can be recombinant.

DETAILED DESCRIPTION OF THE INVENTION

General Definitions

Figure 1:
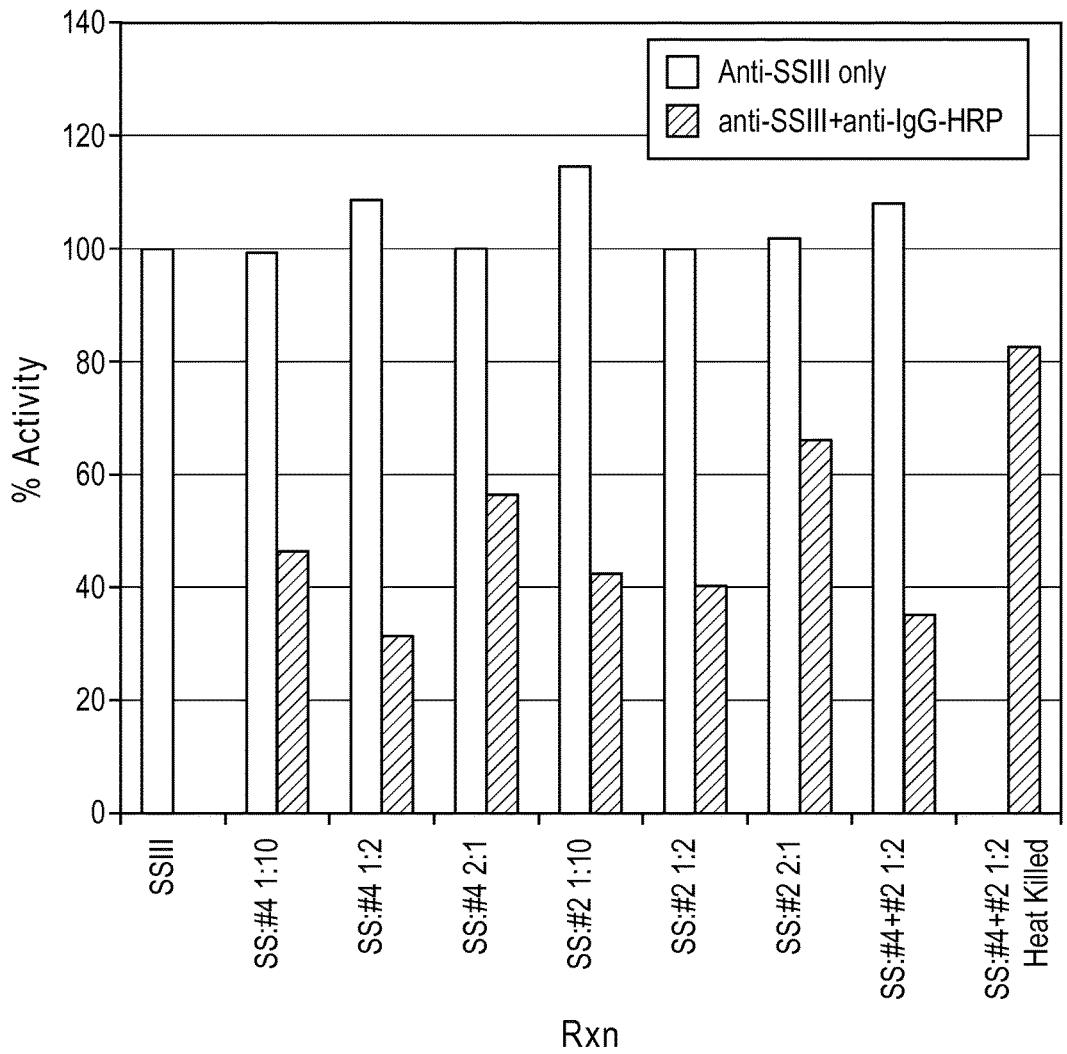
FIG. 1. Bar graph showing the effect of multicomponent inhibitors on SSIII activity. SSIII activity is depicted in the presence of each specified anti-SSIII primary antibody alone (light bars) or with anti-SSIII primary antibody plus goat anti-mouse-IgG-horse radish peroxidase (dark bars). All other activities are normalized to reaction 1. Column 1: No primary mAb or inhibitor components. SSIII activity set to 100% by definition. Columns 2-9: Anti-SSIII mAb clone #4 in molar ratios of SSIII: mAb clone #4 of 1:10 to 2:1. Columns 10-15: Anti-SSIII mAb clone #2 in molar ratios of SSIII: mAb clone #2 of 1:10 to 2:1. Columns 16-17: Anti-SSIII mAb clones #2 and #4 in molar ratios of SSIII: mAb clones #2 and #4 of 1:2. Column 18: Anti-SSIII mAb clones #2 and #4 in molar ratios of SSIII: mAb clones #2 and #4 of 1:2, where the anti-SSIII mAbs were heated to 96° for 7 minutes prior to adding to the SSIII.

"A," "An" and "One" include both the singular and plural, unless otherwise indicated or unless it is clear from the context in which the term is used that one or the other is intended.

"About" refers to a value that is within plus or minus 10% of a reference value. For example, a value of about 50° C. would encompass a range of values between 45° C. and 55° C.

"Amplification" refers to any in vitro method for increasing the number of copies of a nucleotide sequence with the use of a polymerase. Amplification results in the incorporation of nucleotides into a nucleic acid (e.g., DNA) molecule or primer thereby forming a new nucleic acid molecule complementary to the nucleic acid template. Typically, the template and newly formed nucleic acid molecule can be used as templates to synthesize additional nucleic acid molecules. As used herein, one amplification reaction may consist of many rounds of nucleic acid synthesis. Amplification reactions include, for example, polymerase chain reactions (PCR). One PCR-type amplification may consist of 5 to 100 or more rounds of denaturation and synthesis of a nucleic acid molecule.

"Antibody" refers to molecule(s) that are capable of binding an epitope or antigenic determinant. The term is meant to include whole antibodies and antigen-binding fragments thereof, including Fab, Fab' and F(ab')2, Fd, single-chain Fvs (scFv), single-chain antibodies, disulfide-linked Fvs (sdFv) and fragments comprising either a $V_L$ or $V_H$ domain. The antibodies can be from any animal origin including birds such as chicken, and mammals such as human, murine, rat, rabbit, goat, guinea pig, sheep, cow, camel and horse. The term "antibodies" also includes genetically prepared equivalents thereof, and chemically or genetically prepared fragments of antibodies (such as Fab fragments), recombinant antibodies, chimeric antibodies, monoclonal, polyclonal, affinity purified polyclonal, and the like. Antibodies and fragments thereof, can be used singly or in mixtures in the practice of this invention.

"Bound" means to be coupled via covalent or non-covalent interactions. Covalent binding can occur via chemically coupling and the formation of, e.g., ester, ether, phosphoester, thioester, thioether, urethane, amide, amine, peptide, imide, hydrazone, hydrazide, carbon-sulfur, carbon-phosphorus, and like bonds. Non-covalent binding can occur via, e.g., ionic interactions, hydrophobic interactions, hydrogen bonds, etc.

"Exonuclease activity" relates to enzymatic activity resulting in the removal of nucleotides from a polynucleotide, in either the 3'-to-5' direction ("3'-to-5' exonuclease activity") or the 5'-to-3' direction ("5'-to-3' exonuclease activity"). A polymerase may exhibit either or both 3'-to-5' and 5'-to-3' exonuclease activity. Modified or recombinant polymerases are available in which either or both have been substantially reduced or eliminated.

"Hybridization" and "hybridizing" refer to the pairing of two complementary single-stranded nucleic acid molecules (RNA and/or DNA) to give a double-stranded molecule. Two nucleic acid molecules may be hybridized, although the base pairing is not completely complementary. Accordingly, mismatched bases do not prevent hybridization of two nucleic acid molecules provided that appropriate conditions, well known in the art, are used. Hybridization refers in some contexts to pairing of an oligonucleotide with a DNA template molecule.

"Inactivated" refers to a reduction of a specified property or activity to less than 10%, 7.5%, 5%, 2.5%, 1%, 0.5% or 0.1% of its original property or activity including the polymerase activity of a polymerase or the inhibitory activity of an inhibitor.

"Nucleotide" refers to a base-sugar-phosphate combination. Nucleotides are monomeric units of a nucleic acid (DNA and RNA). The term nucleotide includes deoxyribonucleoside triphosphates ("dNTPs"), such as dATP, dCTP, dITP, dUTP, dGTP, dTTP, or derivatives thereof. Such derivatives include, for example, [αS]dATP, 7-deaza-dGTP and 7-deaza-dATP. The term nucleotide also includes dideoxyribonucleoside triphosphates ("ddNTPs") and their derivatives, such as ddATP, ddCTP, ddGTP, ddITP, and ddTTP. The term nucleotide also includes ribonucleoside triphosphates (rNTPs) such as rATP, rCTP, rITP, rUTP, rGTP, rTTP and their derivatives, which are analogous to the above-described dNTPs and ddNTPs except that the rNTPs comprise ribose instead of deoxyribose or dideoxyribose in their sugar-phosphate backbone. The term "NTP" is more general and may encompass rNTP, dNTP, ddNTP or nucleotide analogs. A "nucleotide" may be unlabeled or detectably labeled by well known techniques. Detectable labels include, for example, radioactive isotopes, fluorescent labels, chemiluminescent labels, bioluminescent labels and enzyme labels.

"Nucleic acid" and "Nucleic acid molecule" refer to a series of contiguous nucleotides which may encode a full-length polypeptide or a fragment of any length thereof, or which may be non-coding.

"Nucleic acid polymerase" and "Polymerase" refer to any polypeptide, protein or enzyme with nucleic acid polymerase activity.

"Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

"Polymerase activity" is an enzymatic activity, whereby a polymerase synthesizes polynucleotides in the 5' to 3' direction by addition of a new nucleotide to the 3' end of a the previous nucleotide, according to an RNA or DNA template that directs the synthesis of the polynucleotide. For example, a DNA polymerase can synthesize the formation of a DNA molecule complementary to a single-stranded DNA or RNA template by extending a primer in the 5'-to-3' direction. Polymerases include DNA-dependant DNA polymerases; DNA-dependant RNA polymerases, also known as transcriptases; RNA-dependant DNA polymerases, also known as reverse transcriptases; and, more often seen in certain viruses, RNA-dependant RNA polymerases. A given polymerase enzyme may have more than one polymerase activity. For example, some DNA-dependent DNA polymerases, such as Taq, also exhibit reverse transcriptase polymerase activity.

"Polypeptide," "Peptide" and "Protein" refer to series of contiguous amino acids, of any length.

"Primer" refers to a single-stranded oligonucleotide that is extended by covalent bonding of nucleotide monomers during amplification or polymerization of a DNA molecule.

"Stable" and "Stability" refer to the retention by an enzyme of at least about 70%, at least about 80%, or at least about 90%, of the original enzymatic activity (in units) after the enzyme or composition containing the enzyme has been subjected to a condition which might otherwise have resulted in loss of activity for an enzyme that was not stable. Labile is the opposite of stable.

"Substantially pure" means that the desired purified molecule such as a protein or nucleic acid is essentially free from contaminants typically associated with the desired molecule. Contaminating components include compounds or molecules that may interfere with the inhibitory or synthesis reactions of the invention, and/or that degrade or digest the molecules of the invention and/or that degrade or digest the synthesized or amplified nucleic acid molecules produced by the methods of the invention.

"Template" refers to a double-stranded or single-stranded nucleic acid molecule that is to be amplified, synthesized or sequenced. In the case of a double-stranded RNA or DNA molecule, denaturation of its strands to form a first and a second strand is performed before these molecules may be amplified, synthesized or sequenced. A primer complementary to a portion of a template is hybridized to the template under appropriate conditions and a polymerase of the invention may then synthesize a nucleic acid molecule complementary to the template or a portion thereof. The newly synthesized DNA molecule, according to the invention, may be equal or shorter in length than the original DNA template. Mismatch incorporation or strand slippage during the synthesis or extension of the newly synthesized DNA molecule may result in one or a number of mismatched base pairs. Thus, the synthesized nucleic acid molecule need not be exactly complementary to the template.

"Thermostable" refers to an enzyme (such as a polypeptide having polymerase activity) that is resistant to inactivation by heat. A "thermostable" enzyme is in contrast to a "thermolabile" polymerase, which can be inactivated by heat treatment. Thermolabile proteins can be inactivated at physiological temperatures, and can be categorized as meso-thermostable (inactivation at about 45° C. to 65° C.), and a thermostable (inactivation greater than about 65° C.). For example, the activities of the thermolabile T5 and T7 DNA polymerases can be totally inactivated by exposing the enzymes to a temperature of about 90° C. for about 30 seconds. A thermostable polymerase activity is more resistant to heat inactivation than a thermolabile polymerase. However, a thermostable polymerase does not mean to refer to an enzyme that is totally resistant to heat inactivation; thus heat treatment may reduce the polymerase activity to some extent. A thermostable polymerase typically will also have a higher optimum temperature than thermolabile DNA polymerases.

"Unit" refers to the activity of an enzyme. When referring to a thermostable polymerase (e.g., Taq and Pfx), one unit of activity is the amount of enzyme that will incorporate 10 nanomoles of NTPs into acid-insoluble material (i.e., DNA or RNA) in 30 minutes under standard primed DNA synthesis conditions at 74° C. When referring to reverse transcriptases (e.g. SuperScript III), one unit is defined as the amount of enzyme which incorporates 1 nmole of dTTP into acid insoluble material in 10 min at 37° C.

"Working concentration" refers to the concentration of a reagent that is at or near the optimal concentration used in a solution to perform a particular function (such as amplification or digestion of a nucleic acid molecule). The working concentration of a reagent is also described equivalently as a "1× concentration" or a "1× solution" (if the reagent is in solution) of the reagent. Accordingly, higher concentrations of the reagent may also be described based on the working concentration; for example, a "2× concentration" or a "2× solution" of a reagent is defined as a concentration or solution that is twice as high as the working concentration of the reagent; a "5× concentration" or a "5× solution" is five times as high as the working concentration of the reagent; and so on.

Compositions

Multi-Component Polymerase Inhibitors

The invention provides multi-component inhibitors that include a polymerase-binding molecule (PBM) and a PBM-binding molecule or complex, where binding of the PBM to a polymerase does not substantially inhibit the polymerase activity of the polymerase, but where binding of the PBM and PBM-binding molecule/complex together substantially inhibit the polymerase activity of the polymerase. Such multi-component polymerase inhibitors may also inhibit the 3'-5' exonuclease activity, 5'-3' exonuclease activity and/or RNase H activity of a polymerase.

The PBM does not substantially inhibit the polymerase activity of a polymerase in the absence of the PBM-binding molecule/complex. Accordingly, a polymerase bound by a PBM in the absence of a PBM-binding molecule/complex exhibits at least about 70%, 75%, 80%, 85%, 90%, 95%, 97.5%, 99%, 99.75%, 100% or >100% of the polymerase activity observed in the absence of the PBM.

Binding of a PBM together with a PBM-binding molecule/complex substantially inhibits the polymerase activity of a polymerase. Accordingly, a polymerase bound by a PBM in the presence of a PBM-binding molecule/complex exhibits less than about 30%, 25%, 20%, 15%, 10%, 5%, 2.5% 1% or 0.25% of the polymerase activity observed either in the absence of both the PBM and PBM-binding molecule/complex, or in the presence of the PBM but in the absence of the PBM-binding molecule/complex.

Polymerase inhibition by a PBM and PBM-binding molecule/complex may be irreversible or reversible. Inhibition of polymerase activity may be reversed by any means known in the art including, e.g., dilution, competition, physical or ionic disruption, or temperature change. For example, heating a composition containing a polymerase, PBM and PBM-binding molecule/complex may reverse polymerase inhibition. Such heating typically involves a shift to a higher temperature that does not substantially reduce the polymerase's polymerase activity (e.g., temperatures up to 40° C., 50° C., 55° C., 60° C., 65° C., 70° C., 75° C., 80° C., 90° C., 95° C. or 99° C.). Such heating may be sufficient to cause denaturation of the PBM (e.g., antibody); denaturation of the PBM-binding molecule/complex; dissociation of the PBM from the nucleic acid polymerase; dissociation of the PBM-binding molecule/complex from the PBM; dissociation of a PBM-binding complex, or a combination of these effects.

Polymerase Binding Molecules (PBMs)

A PBM can be an antibody, antibody fragment, chemical compound, acid, antibiotic, heavy metal, metal chelator, nucleotide analog, sulfhydryl reagent, anionic detergent, polyanion, captan ((N-[trichloromethyl]-thio)-4-cyclohexene-1,2-dicarboximide), acidic polysaccharide or lectin.

A PBM can be specific for a DNA-dependent a DNA polymerase, a DNA-dependent RNA polymerase, a RNA-dependent DNA polymerase (reverse transcriptase) and/or a RNA-dependent RNA polymerase. Thus, compositions in accord with the invention can include a PBM that binds a DNA polymerase such as Taq DNA polymerase, Tzi DNA polymerase, Tne DNA polymerase, Tma DNA polymerase, Pfu DNA polymerase, Tfl DNA polymerase, Tth DNA polymerase, Pwo DNA polymerase, Bst DNA polymerase, Bca DNA polymerase, VENT™ DNA polymerase, DEEP-VENT™ DNA polymerase, T7 DNA polymerase, T5 DNA polymerase, DNA polymerase III, Klenow fragment DNA polymerase, Stoffel fragment DNA polymerase, and/or mutants, fragments or derivatives thereof. Compositions in accord with the invention also can include a PBM that binds a polymerase having reverse transcriptase activity, such as an M-MLV reverse transcriptase, an RSV reverse transcriptase, an AMV reverse transcriptase, an RAV reverse transcriptase, an MAV reverse transcriptase, an HIV reverse transcriptase (any of which may be reduced in, substantially reduced in, or have no detectable RNase H activity) and/or mutants, fragments or derivatives thereof.

Compositions in accord with the invention can include a PBM that binds to a thermolabile polymerase, and/or to a thermostable nucleic acid polymerase, such as a *Thermus aquaticus* polymerase, a *Thermus thermophilus* polymerase, a *Thermus filiformis* polymerase, a *Thermus flavus* polymerase, a *Pyrococcus furiosus* polymerase, a *Thermococcus litoralis, Thermococcus zilligi* or a *Thermotoga* species polymerase, or a recombinant variant thereof.

Certain exemplary compositions of the invention include antibody PBMs ("PBAs"). Accordingly, the invention provides compositions that include a polymerase-binding antibody (PBA) or derivative and a PBA-binding molecule/complex, where binding of the PBA or derivative to a polymerase does not substantially inhibit the polymerase activity of the polymerase, but where binding of the PBA and PBA-binding molecule/complex together substantially inhibit the polymerase activity of the polymerase.

A PBA can be a monoclonal antibody, a polyclonal antibody, an Fc antibody fragment, a chimeric antibody or a recombinant or other derivative thereof. A PBA can be an IgA antibody, an IgG antibody, an IgM antibody, an IgD antibody, an IgE antibody, an IgY antibody, an IgE antibody or fragment thereof. Specific monoclonal PBAs include: Anti-SSIII mAb clone #4, Anti-SSIII mAb clone #2, Primary anti-Tzi antibody clone 8C9, Primary anti-Tzi antibody clone 3B11.2, Primary anti-Tzi antibody clone 8F3.2, Primary anti-Tzi antibody clone 9G2.2, Primary anti-Tzi antibody clone 802.2, Primary anti-Tzi antibody clone 10F7.3, Primary anti-Tzi mAb clone 1G11.3, anti-Thermo-Script mAb DE11, anti-RT41A mAb #5, anti-RT41A mAb #10, anti-Taq mAb #5 and anti-Taq mAb #10.

PBM-Binding Molecules/Complexes

A PBM-binding molecule/complex can be any molecule/complex known in the art to be capable of binding a PBM.

When the PBM is an antibody (i.e., a PBA), the PBM-binding molecule/complex is capable of binding an antibody, and can be referred to as a PBA-binding molecule/complex. Many molecules/complexes capable of binding antibodies are known to those skilled in the art. Thus, a PBA-binding molecule/complex can include an antibody, an antibody fragment (e.g., Fab fragment), protein G, protein A, a derivatized antibody, a derivatized protein G, a derivatized protein A, protein H, ARP or a complex including any of the foregoing with another moiety.

In some embodiments, a PBA-binding molecule/complex comprises an antibody. The antibody may be monoclonal, polyclonal, chimeric, or an Fc fragment. The antibody may also be recombinant. In another embodiment, the antibody may be IgA, IgG, IgM, IgE, IgY, IgD or derivative thereof. A PBA-binding antibody may be from any species (including humans, monkeys, mice, rats, rabbits, horses, goats, sheep, cows, pigs, chickens, fish, etc.) and may bind to antibodies from any species (including humans, monkeys, mice, rats, rabbits, horses, goats, sheep, cows, pigs, chickens, fish, etc.). PBA-binding antibodies may be derivatized or underivatized monoclonal antibodies, derivatized or underivatized polyclonal antibodies, derivatized or underivatized Fc or Fab antibody fragments, derivatized or underivatized chimeric antibodies, or derivatized or underivatized recombinant antibodies. PBA-binding antibodies can be IgA, IgG, IgM, IgD, IgE, IgY antibodies or fragments or derivatives thereof.

In some embodiments, a PBA-binding molecule/complex comprises a bacterial immunoglobulin binding protein (IgBP) such as, e.g., *Staphylococcus aureus* protein A, which binds to all immunoglobulin molecules, and streptococcal protein G, which binds specifically to IgG. Other bacterial IgBPs are also available and may be used in the compositions and methods described herein including, for example, *Haemophilus somnus* high molecular weight IgBPs, and *Peptostreptococcus magnus* protein L, which binds immunoglobulin (Ig) light chains. A variety of eukaryotic antibody-binding proteins may also be used, such as Fc receptors on cells of the immune system. In addition, other immunoglobulin binding proteins may be used, including sir22 (Stenberg et al., *J. Biol. Chem.* 269:13458-13464, 1994), sibA (Fagan et al., *Infect. Immun.* 69:4851-4857, 2001) and ARP (U.S. Pat. No. 5,180,810; European Patent Application No. 0367890 A1).

PBM-binding molecules (including PBA-binding molecules such as antibodies) and molecules comprising PBM-binding complexes, may be derivatized with one or more molecules or moieties using well-known procedures, such as chemical coupling or recombinant DNA technology. Derivatization moieties include, e.g., detectable labels, signaling groups, proteins, chemical groups, ligands, haptens or polymers. A detectable label can be enzymatic, chemiluminescent, bioluminescent, radioactive or fluorescent. Exemplary detectable labels include rhodamine, biotin, fluorescein, horseradish peroxidase, alkaline phosphatase, and AlexaFluor488. Exemplary derivatization proteins include horseradish peroxidase, alkaline phosphatase, protein G, and albumin. Exemplary derivatization polymers include polyethylene glycol, polyoxyethylene, polyoxypropylene, and polyoxyethylene/polyoxypropylene copolymer.

Derivatization typically alters the properties of a PBM-binding molecule. For example, large moieties including polymers, proteins and large chemical groups will increase the bulkiness of a PBM-binding molecule/complex. Attached moieties may also alter the net charge, solubility, ionic strength or other physical or chemical property of a PBM. Attached moieties may also serve as targets for other binding molecules.

PBM-binding molecules and PBM-binding complexes of molecules may be used in the compositions and methods described herein. By way of example, a PBA-binding complex may include a PBA-binding antibody, to which is bound Protein G. Other exemplary PBA-binding complexes include an antibody coupled to horseradish peroxidase; an antibody-protein G-horseradish peroxidase complex; a protein G-AlexaFluor488 complex; and an antibody-biotinstreptavidin complex. Yet another exemplary PBA-binding complexes include a PBA-binding antibody derivatized with a hapten, which can bind an antibody against the hapten. In this manner, the number of antibodies, moieties and the like associated with a given target polymerase to be inhibited can be varied as desired.

Polymerases

In addition to a PBM and/or PBM-binding molecule/complex, compositions of the invention may include one or more DNA and/or RNA polymerases. The polymerases may be thermolabile or thermostable. DNA polymerases include, but are not limited to, *Thermus thermophilus* (Tth) DNA polymerase, *Thermus aquaticus* (Taq) DNA polymerase, *Thermococcus zilligi* (Tzi), *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Pyrococcus* sp KOD2 DNA polymerase, *Bacillus stearothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Thermococcus kodakaraensis* DNA polymerase, *Methanobacterium thermoautotrophicum* (Mth) DNA polymerase, a *mycobacterium* DNA polymerase (e.g. Mtb, Mlep); and generally Pol I and Pol III type polymerases.

In one embodiment, DNA polymerase from *Thermus filiformis* strain RT41A is used in the compositions and methods described herein. Nucleotide and protein sequences corresponding to Tfi DNA polymerases are disclosed in SEQ ID NOS: 9 and 21; Jung, et al., 1997, Mol. Cells, 7(6):769-76; GenBank Accession Numbers AF030320 and AAC46079; WO03/025132 and copending U.S. patent application Ser. No. 10/244,081, the contents of which are incorporated herein by reference. Isolation and characterization of Tzi polymerase is described in copending U.S. Provisional Patent Application Ser. No. 60/647,408, entitled "DNA Polymerase from *Thermococcus zilligi* and Mutants Thereof" listing inventors Jun. E. Lee, Kyusung Park, Katherine R. Griffiths, Moreland D. Gibbs, and Peter L. Bergquist, filed on the same date as the present application, the entire contents of which are incorporated herein by reference.

RNA polymerases suitable for use in the compositions and methods described herein include any enzyme having RNA polymerase activity, including both DNA-dependent and RNA-dependant RNA polymerases. More typically, RNA polymerases used in the present invention will be DNA-dependent RNA polymerases, also known as reverse transcriptases. Transcriptases may be isolated from any source, including *E. coli*, T3, T5, SP-6, T7 and *Xenopus*, and mutants, variants and derivatives thereof.

Reverse transcriptases include any enzyme having reverse transcriptase activity. Such enzymes include, but are not limited to, retroviral reverse transcriptase (e.g., Moloney Murine Leukemia Virus (M-MLV), Avian Myeloblastosis Virus (AMV) or Rous Sarcoma Virus (RSV) reverse transcriptases), Superscript I®, Superscript II®, Superscript III®, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al, *Science* 239:487-491 (1988); U.S. Pat. Nos. 4,889,818 and 4,965,188; Shandilya et al., *Extremophiles* 8(3):243-251, 2004), Tne DNA polymerase (WO 96/10640 and WO 97/09451), Tma DNA polymerase (U.S. Pat. No. 5,374,553) and mutants, variants or derivatives thereof (see, e.g., WO 97/09451 and WO 98/47912).

In one embodiment, reverse transcriptases include those that have reduced, substantially reduced or eliminated RNase H activity. By an enzyme "substantially reduced in RNase H activity" is meant that the enzyme has less than about 20%, 15%, 10%, 5%, or 2%, of the RNase H activity of the corresponding wild type or RNase H+ enzyme such as wild type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al, *Nucl. Acids Res.* 16:265 (1988) and in Gerard, G. F., et al., *FOCUS* 14(5):91 (1992), the disclosures of all of which are fully incorporated herein by reference. Polypeptides suitable for use in the compositions and methods described herein include, but are not limited to, M-MLV H$^-$ reverse transcriptase, RSV H$^-$ reverse transcriptase, AMV H$^-$ reverse transcriptase, RAV (Rous-associated virus) H$^-$ reverse transcriptase, MAV (myeloblastosis-associated virus) H$^-$ reverse transcriptase and HIV H$^-$ reverse transcriptase (See U.S. Pat. No. 5,244,797 and WO 98/47912), and superscript III. It will be understood by one of ordinary skill, however, that any enzyme capable of producing a DNA molecule from a ribonucleic acid molecule (i.e., having reverse transcriptase activity) may be equivalently used in the compositions, methods and kits described herein, including those described in PCT WO03/025132, the entire disclosure of which is incorporated herein by reference.

The enzymes having polymerase may be obtained commercially, for example from Invitrogen (Carlsbad, Calif.), Perkin-Elmer (Branchburg, N.J.), New England BioLabs (Beverly, Mass.) or Boehringer Mannheim Biochemicals (Indianapolis, Ind.). Alternatively, polymerases or reverse transcriptases having polymerase activity may be isolated from their natural viral or bacterial sources according to standard procedures for isolating and purifying natural proteins that are well-known to one of ordinary skill in the art (see, e.g., Houts, G. E., et al., *J. Virol.* 29:517 (1979)). In addition, such polymerases/reverse transcriptases may be prepared by routine recombinant DNA techniques well know to those skilled in the art (see, e.g., Kotewicz, M. L., et al., *Nucl. Acids Res.* 16:265 (1988); U.S. Pat. No. 5,244,797; WO 98/47912; Soltis, D. A., and Skalka, A. M., *Proc. Natl. Acad. Sci.* USA 85:3372-3376 (1988)).

Recombinant, mutants and other variants of the polymerases described herein may also be used. Recombinant variants may be particularly useful in some embodiments described herein. For example, using recombinant DNA technology, skilled artisans can generate a polymerase that contains an amino acid epitope that is the target of a polymerase-binding antibody. Alternatively, or in addition, the epitope could bind other molecules such as ligands, receptors, haptens and the like. As a result, by adding a particular epitope to several polymerases, it is possible to inhibit a range of different polymerases with a single PBM in the presence of a PBM-binding molecule/complex. In another embodiment, the conditions under which a given polymerase is inhibited by a given inhibitor can be optimized by modifying the inhibitor and/or, through recombinant technologies, the polymerase.

Antibodies

PBAs and PBA-binding antibodies may be polyclonal or monoclonal, and may be prepared by any of a variety of methods (see, e.g., U.S. Pat. No. 5,587,287). For example, polyclonal antibodies may be made by immunizing an animal with one or more polypeptides having polymerase activity or portions thereof according to standard techniques (see, e.g., Harlow, E., and Lane, D., *Antibodies: A Laboratory Manual*, Cold Spring Harbor, N.Y.: Cold Spring Harbor Laboratory Press (1988); Kaufman, P. B., et al., In: *Handbook of Molecular and Cellular Methods in Biology and Medicine*, Boca Raton, Fla.: CRC Press, pp. 468-469 (1995)). Alternatively, anti-polymerase monoclonal antibodies (or fragments thereof) may be prepared using hybridoma technology that is well-known in the art (Köhler et al., *Nature* 256:495 (1975); Köhler et al., *Eur. J. Immunol.* 6:511 (1976); Köhler et al., *Eur. J. Immunol.* 6:292 (1976); Hammerling et al., In: *Monoclonal Antibodies and T-Cell Hybridomas*, New York: Elsevier, pp. 563-681 (1981); Kaufman, P. B., et al., In: *Handbook of Molecular and Cellular Methods in Biology and Medicine*, Boca Raton, Fla.: CRC Press, pp. 444-467 (1995)). Monoclonal PBAs typically have a polymerase association constant of at least about $10^7$ molar$^{-1}$, although antibodies having lower affinities may also be used.

Exemplary antibodies include: Anti-SSIII mAb clone #4; Anti-SSIII mAb clone #2; Primary anti-Tzi antibody clone 8C9; Primary anti-Tzi antibody clone 3B11.2; Primary anti-Tzi antibody clone 8F3.2; Primary anti-Tzi antibody clone 9G2.2; Primary anti-Tzi antibody clone 802.2; Primary anti-Tzi antibody clone 10F7.3; Primary anti-Tzi mAb clone 1G11.3; anti-ThermoScript mAb DE11; Primary anti-Tzi antibody clone 9G3.3, Primary anti-Tzi antibody clone 6F3.3, anti-RT41A mAb #5, anti-RT41A mAb #10, anti-Taq mAb #5 and anti-Taq mAb #10.

It will be appreciated that Fab, F(ab')$_2$ and other fragments of the above-described antibodies may be used in the methods described herein. Such fragments are typically produced by proteolytic cleavage, using enzymes such as papain (to produce Fab fragments) or pepsin (to produce F(ab')$_2$ fragments). Antibody fragments may also be produced through the application of recombinant DNA technology or through synthetic chemistry.

Formulation of Compositions

Compositions of the invention can include, in addition to a PBM and a PBM-binding molecule/complex, one or more polymerases. Some such compositions include one or more thermostable polymerases in addition to a PBM and a PBM-binding molecule. Compositions can be formulated such that after reversal of polymerase inhibition by a PBM and PBM-binding molecule/complex, 0.5 to 1,000 units/ml of DNA-directed DNA polymerase activity (e.g., 0.5 to 100, 0.5 to 50, 0.5 to 20, 0.5 to 10, and 0.5 to 5) and/or 20 to 100,000 units/ml of reverse transcriptase activity (e.g., 50 to 500, 200 to 2,000, and 1,000 to 20,000) are present in a reaction. As an example, about 0.5 to about 20 units of polymerase per ml of PCR reaction mixture is available upon reversal of polymerase inhibition by a PBM and PBM-binding molecule/complex. Other suitable concentrations of reverse transcriptase enzymes and nucleic acid polymerases will be apparent to one of ordinary skill in the art.

PBMs and PBM-binding molecule/complex can be provided in a composition comprising a polymerase at a molar ratio of 0.1 to about 100 (e.g., 0.5 to 5, or 2 to 20) moles per mole of DNA polymerase. In one embodiment, about 1 to about 3 moles of PBM and/or PBM-binding molecule/complex per mole of DNA polymerase is used.

Compositions in accord with the invention also can include one or more DNA modifying enzymes (e.g., ligase, kinase, phosphatase, nuclease, endonuclease, exonuclease, topoisomerase, gyrase, terminal deoxynucleotidyl transferase), nucleic acid templates, nucleic acid primers, nucleic acid substrates (e.g., rATP, rCTP, rGTP, rTTP, rUTP, rITP, dATP, dCTP, dGTP, dTTP, dUTP, dITP, ddATP, ddCTP, ddGTP, ddTTP, ddUTP, ddITP, and derivatives thereof, including labeled nucleosides and nucleotides), detectable nucleic acid primers, and combinations thereof.

Compositions of the invention also can include one or more detergents (e.g., TRITON X-100®, Nonidet P-40, Tween 20, Brij 35, sodium deoxycholate and sodium dodecylsulfate), enzyme cofactors, buffers (e.g., tris(hydroxymethyl)aminomethane, N,N-bis(2-hydroxyethyl)-2-aminoethanesulfonic acid, 4-(2-hydroxyethyl)-1-piperazinethanesulfonic acid, N-(2-hydroxyethyl)piperazine-N'-(2-hydroxypropanesulfonic acid), 3-(N-morpholino)propanesulfonic acid and N[tris(hydroxymethyl)methyl]-2-aminoethanesulfonic acid, phosphate salts (such as sodium phosphate (mono- or dibasic) and potassium phosphate), sodium bicarbonate, and sodium acetate. Ammonium sulfate, magnesium salt (e.g., magnesium chloride and magnesium sulfate), manganese salt (e.g., manganese sulfate) and potassium salts (e.g., potassium chloride) also may be included in compositions of the invention. One or more chelating agents such as ethylenediaminetetraacetate (EDTA) may also be included (e.g., at a concentration of about 0.1 millimolar).

Compositions of the invention generally are at a pH in the range of from about 7.5 to about 9.5 (e.g., at a pH of from about 8 to about 9).

Compositions may be formulated at working concentrations, or in solutions of higher reagent concentrations (e.g., 2×, 2.5×, 5×, 10×, 20×, 25×, 50×, 100×, 250×, 500× and 1000×) that may then be diluted before use.

Methods

The invention provides methods involving the use of compositions that contain a PBM and a PBM-binding molecule/complex, e.g., to inhibit a polymerase. The compositions described herein are particularly useful for nucleic acid synthesis, sequencing, amplification, and cloning. Such methods typically involve bringing a polymerase into contact with a PBM (e.g., PBA) and a PBM-binding molecule/complex, where binding of the PBM to the polymerase does not substantially inhibit the polymerase activity of the polymerase, but where binding of the PBM and PBM-binding molecule/complex together substantially inhibit the polymerase activity of the polymerase. Methods of the invention may also involve reversing inhibition caused by a PBM and PBM-binding molecule/complex.

Nucleic Acid Synthesis, Amplification and Sequencing

The compositions described herein are particularly useful in methods for synthesizing, amplifying and sequencing nucleic acid molecules. Nucleic acid synthesis methods of the invention can be used to make any nucleic acid molecule from DNA or RNA templates, including DNA molecules, RNA molecules, or hybrid DNA/RNA molecules, and of which may be double-stranded or single-stranded. As such, the methods and/or compositions of the invention may be used in any technique including, but not limited to, primer extension, transcription, amplification, PCR, reverse transcription, sequencing and the like.

Nucleic acid synthesis and amplification methods in which the present compositions may be used include PCR®

(U.S. Pat. Nos. 4,683,195 and 4,683,202), Strand Displacement Amplification (SDA; U.S. Pat. No. 5,455,166; EP 0 684 315), Nucleic Acid Sequence-Based Amplification (NASBA; U.S. Pat. No. 5,409,818; EP 0 329 822), and Abortive Transcription (Published U.S. Patent Application No. 2003/0099950-A1). Nucleic acid sequencing techniques include dideoxy sequencing methods such as those disclosed in U.S. Pat. Nos. 4,962,022 and 5,498,523, as well as more complex PCR-based nucleic acid fingerprinting techniques such as Random Amplified Polymorphic DNA (RAPD) analysis (Williams, J. G. K., et al., *Nucl. Acids Res.* 18(22): 6531-6535, 1990), Arbitrarily Primed PCR (AP-PCR; Welsh, J., and McClelland, M., *Nucl. Acids Res.* 18(24): 7213-7218, 1990), DNA Amplification Fingerprinting (DAF; Caetano-Anollés et al., *Bio/Technology* 9:553-557, 1991), microsatellite PCR or Directed Amplification of Minisatellite-region DNA (DAMD; Heath, D. D., et al., *Nucl. Acids Res.* 21(24): 5782-5785, 1993), and Amplification Fragment Length Polymorphism (AFLP) analysis (EP 0 534 858; Vos, P., et al., *Nucl. Acids Res.* 23(21):4407-4414, 1995; Lin, J. J., and Kuo, J., *FOCUS* 17(2):66-70, 1995).

Nucleic acid amplification methods comprise contacting a nucleic acid molecule to be amplified with one or more of the compositions described herein, thus providing a population of amplified copies of the nucleic acid molecule. Nucleic acid sequencing methods comprise contacting the nucleic acid molecule to be sequenced with one or more of the compositions described herein. According to these methods, amplification and sequencing of the nucleic acid molecule may be accomplished by any of the above-described amplification and sequencing techniques. In one embodiment, amplification and sequencing is performed by PCR. The present amplification and sequencing methods may be used for amplification and sequencing of nucleic acid molecules between about 0.5 and 7 kb, 0.5-5 kb, 1-5 kb, 1-3 kb or 1-2 kb.

Nucleic acid synthesis, amplification and sequencing methods typically involve contacting a template nucleic acid with a composition comprising a polymerase (e.g., thermostable polymerase), a PBM, a PBM-binding molecule/complex, and nucleotide substrates under conditions where the polymerase activity of the polymerase is inhibited. Such reaction mixtures typically include a nucleic acid primer as well. Such nucleic acid synthesis, amplification and sequencing methods typically involve bringing such reaction mixtures to a condition (e.g., higher temperature) that is sufficient to reverse inhibition of the polymerase but that does not substantially reduce the polymerase's polymerase activity. For example, such inhibition reversal may be accomplished by shifting a reaction mixture to a temperature up to 40° C., 50° C., 55° C., 60° C., 65° C., 70° C., 75° C., 80° C., 90° C., 95° C. or 99° C. This heating may be sufficient to cause denaturation of the PBM (e.g., antibody); denaturation of the PBM-binding molecule/complex; dissociation of the PBM from the nucleic acid polymerase; dissociation of the PBM-binding molecule/complex from the PBM; dissociation of the PBM-binding molecule/complex, or a combination of these effects.

Cloning

Methods of cloning nucleic acids also are provided. Such cloning methods typically involve synthesizing or amplifying one or more nucleic acid molecules using a polymerase; incubating the synthesized nucleic acids with a PBM and a PBM-binding molecule/complex, such that binding of the PBM to the polymerase does not substantially inhibit the polymerase activity of the polymerase, but such that binding of the PBM and PBM-binding molecule/complex together substantially inhibit the polymerase activity of the polymerase; and inserting the amplified or synthesized nucleic acid molecules into one or more host cells.

The invention provides cloning methods that involve the use of a PBM and PBM-binding molecule, whereby residual polymerase activity remaining in the reaction mixture after nucleic acid amplification or synthesis is inactivated or inhibited. By the methods described herein, amplified, synthesized or digested nucleic acid molecules may be quickly and efficiently ligated (using ligases, topoisomerases, etc.) into cloning vectors, and these vectors then inserted into host cells.

One exemplary cloning method involves: (a) amplifying or synthesizing one more nucleic acid molecules in the presence of one or more polymerases to produce amplified nucleic acid molecules; and (b) incubating the nucleic acid molecules with a PBM and PBM-binding molecule under conditions sufficient to inhibit or inactivate the polymerase activity of the polymerase.

In one embodiment, the amplified nucleic acid fragments may be cloned (ligated) directly into one or more vectors to produce one or more genetic constructs. The genetic constructs then may be transformed into one or more host cells.

In other exemplary cloning methods, amplified molecules cleaved or digested with one or more restriction enzymes or one or more recombination proteins as described in more detail below are cloned into appropriate insertion sites of cloning vectors (see, e.g., Ausubel, F. M., et al., eds., "Current Protocols in Molecular Biology," New York: John Wiley & Sons, Inc., pp. 3.16.1-3.16.11 (1995)). Restriction enzymes used for cleavage of the amplified molecules may include blunt-end cutters (e.g., SmaI, SspI, ScaI, etc.) and sticky-end cutters (e.g., HindIII, BamHI, KpnI, etc.). Such cloning methods also may involve the use of uracil DNA glycosylase ((UDG); see U.S. Pat. No. 5,137,814, which is incorporated herein by reference in its entirety). Such methods typically involve: (a) forming a mixture comprising one or more nucleic acid molecules, one or more PBMs and one or more PBM-binding molecules; and (b) ligating the nucleic acid molecules into one or more of the above-described vectors to form one or more genetic constructs. Analogously, methods suitable for cloning a nucleic acid molecule into one or more vectors typically involve: (a) forming a mixture comprising nucleic acid molecules to be cloned, cloning vectors and one or more polymerase inhibitors; and (b) ligating the nucleic acid molecules into one or more vectors to form one or more genetic constructs. Another exemplary cloning method involves: (a) forming a mixture comprising the nucleic acid molecules to be cloned, one or more PBMs, one or more PBM-binding molecules and one or more restriction endonucleases; and (b) ligating the nucleic acid molecules into one or more of the above-described vectors to form one or more genetic constructs. Another exemplary cloning method involves: (a) forming a mixture comprising the nucleic acid molecules to be cloned, one or more PBMs, one or more PBM-binding molecules, and one or more recombination proteins; and (b) ligating the nucleic acid molecules into one or more of the above-described vectors to form one or more genetic constructs.

The mixture formed in the steps (a) of the above-described methods may further comprise one or more additional components, including, a polymerase, dNTPs or ddNTPs, one or more buffer salts, and the like. A polymerase and restriction endonuclease or recombination protein may be added to the mixture simultaneously, or may be added sequentially, in any order.

The exemplary cloning methods may also comprise one or more additional steps, such as the transformation of one or more of the genetic constructs formed by these methods into host cells.

Target Nucleic Acids

Nucleic acid may be DNA (including cDNA), RNA (including polyadenylated RNA (polyA+RNA), messenger RNA (mRNA), transfer RNA (tRNA) and ribosomal RNA (rRNA)) or DNA-RNA hybrid molecules, and may be single-stranded or double-stranded.

Nucleic acids to be cloned, or to serve as templates for sequencing, synthesis, amplification may be derived from a variety of sources. For example, target nucleic acids may be prepared synthetically according to standard organic chemical synthesis methods that will be familiar to one of ordinary skill or may be obtained from natural sources, such as a variety of cells, tissues, organs or organisms. Nucleic acids and cDNA libraries may be obtained commercially, for example from Invitrogen (Carlsbad, Calif.) and other commercial suppliers that will be familiar to the skilled artisan.

A target nucleic acid may also be extracted in some manner to make it available for contact with the primers and other reagents. This may involve the removal of unwanted proteins and cellular matter from the specimen. Various procedures for doing this are known in the art, including those described by Laure et al in *The Lancet*, pp. 538-540 (Sep. 3, 1988), Maniatis et al, *Molecular Cloning: A Laboratory Manual*, pp. 280-281 (1982), Gross-Belland et al in *Eur. J. Biochem.*, 36, 32 (1973) and U.S. Pat. No. 4,965,188. Extraction of DNA from whole blood or components thereof are described, for example, in EP-A-0 393 744 (published Oct. 24, 1990), Bell et al, *Proc. Natl. Acad. Sci. USA*, 78(9), pp. 5759-5763 (1981) and Saiki et al, *Bio/Technology*, pp. 1008-1012 (1985).

Variations

Variations of the compositions and methods described herein may be performed by one of ordinary skill in the art. For example, in any of the described methods, a PBM and a PBM-binding molecule/complex may be added to a nucleic acid synthesis reaction mixture together or separately. As another example, molecules that comprise a PBA-binding complex may be added to a nucleic acid synthesis reaction mixture together or separately. As yet another example, polymerase inhibition compositions or methods may include or involve two or more PBMs (one or more of which can be an antibody (i.e., PBA)), two or more PBM-binding molecules/complexes (one or more of which can be or include an antibody), and/or two or more polymerases.

EXAMPLE

Multi-Component Inhibition of a DNA-Dependent and RNA-Dependent DNA Polymerases

Materials and Methods

Antibody production: Recombinant SSIII, Tzi, RT41A, and Taq DNA polymerases were produced and purified (Invitrogen) and used to raise monoclonal mouse anti-SSIII, anti-Tzi, anti-RT41A, and anti-Taq antibodies by commercial antibody producers (Chemicon International, Temecula, Calif.; ProSci Incorporated, Poway, Calif.; and Viro Dynamics Corporation, Hawthorne, N.Y.). All antibodies were verified by the manufacturer to be antigen specific by ELISA. Monoclonal antibodies were purified from hybridoma supernatants or ascites fluid using standard protein G chromatography methods.

SuperScript III unit assay: The activity of SSIII with and without PBM-binding molecule/complex inhibitors was measured using a standard MMLV reverse transcriptase filter-binding unit assay. Activity was measured in 25 µl total volume of assay buffer (50 mM Tris-HCl pH8.3, 75 mM KCl, 6 mM $MgCl_2$, 1 mM DTT, 0.5 mM dTTP, 1 mM poly(A)-0.6 mM $d(T)_{25}$, ~20 µCu/ml [$\alpha$-$^{32}$P]dTTP) containing 1 U of SSIII and varying amounts of inhibitory components. Incubations were performed at indicated temperatures for 15 minutes, and terminated by spotting 20 µl of each reaction onto Whatman GF/C fiber filters. Unincorporated label was removed by TCA washes, and incorporation assessed by liquid scintillation.

Tzi, RT41A, and Taq unit assay: The activity of Tzi, RT41A, or Taq with and without PBM-binding molecule/complex inhibitors was measured using a standard DNA polymerase filter-binding unit assay. Activity was measured in 25 µl total volume in assay buffer (25 mM TAPS pH 9.3, 2 mM $MgCl_2$, 50 mM KCl, 1 mM DTT, 0.2 mM dNTP mix, 2.5 µg nicked salmon testes DNA, and 21 µCi/ml [$\alpha$-$^{32}$P] dCTP), containing 0.25 U Tzi, RT41A, or Taq, and varying amounts of inhibitory components. Incubations were performed at indicated temperatures for 15 minutes, and terminated by spotting 20 µl of each reaction onto Whatman GF/C fiber filters. Unincorporated label was removed by TCA washes, and incorporation assessed by liquid scintillation. In some assays, the enzyme-inhibitor mix was pre-incubated for two minutes at varying temperatures to denature the inhibitor, before active units were determined by the standard assay described above.

Tzi and RT41A PCR assay: Yield and specificity of PCR by Tzi and RT41A were determined in standard PCR reactions with and without a mixture of PBM and PBM-binding molecules. 50 µl PCR reactions were assembled in 1×Tzi or Tfi buffer (Invitrogen) with 1-5 units of polymerase, 100 ng of human genomic DNA, 1.5 mM magnesium chloride, 0.2 mM dNTPs, and 0.2 µM each primer. The reactions were then either moved directly to a preheated thermal cycler for PCR, or left at room temperature for 20 minutes before being moved to the thermal cycler. Cycling conditions were: 94° for 2 minutes, then 35 cycles of (94° for 30 seconds, 58-62° for 30 seconds, and 72° for 1 min/kb of desired product). 20 µl of PCR reactions were run on 1.2% agarose gels, and visualized by ethidium bromide staining on an UV transilluminator.

Inhibition of Reverse Transcriptase Activity by Multicomponent Inhibitors

Figure 2:
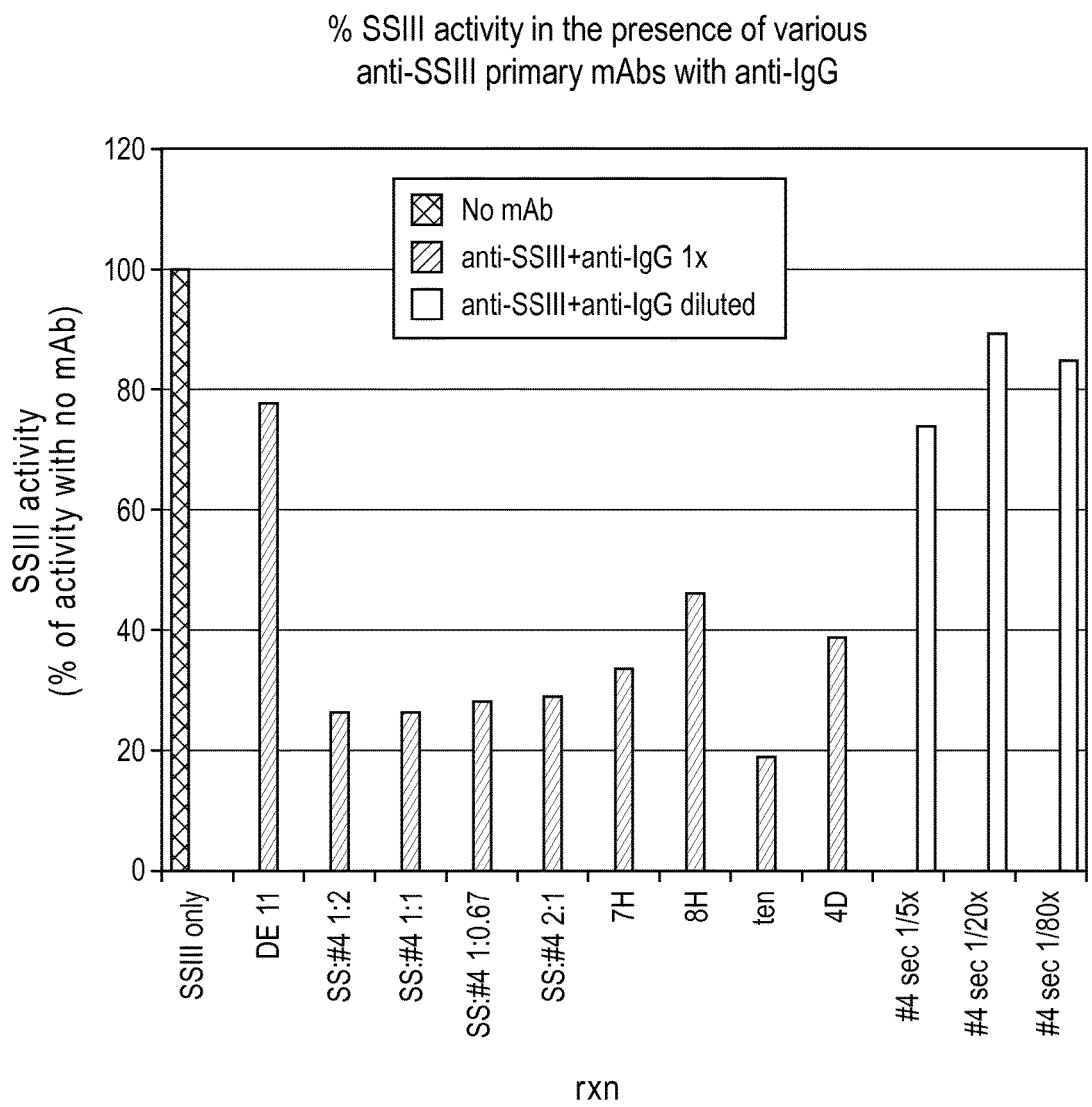
FIG. 2. Bar graph showing SSIII activity in the presence of different anti-SSIII primary mAb, each used as part of a multicomponent inhibitor. SSIII activity in reactions is normalized to that in Column 1. Column 1: No primary mAb or inhibitor components. Activity set to 100% by definition. Column 2: Anti-ThermoScript mAb DE11 with goat-anti-mouse-IgG-horse radish peroxidase. Columns 3-6: Decreasing amounts of anti-SSIII mAb with constant amount of goat-anti-mouse-IgG-horse radish peroxidase. Columns 7-10: Four separate anti-SSIII clones with goat-anti-mouse-IgG-horse radish peroxidase. Columns 11-13: Constant amount of anti-SSIII mAb clone #4 with decreasing amounts of goat-anti-mouse-IgG-horse radish peroxidase.

To determine if SuperScript III (SSIII) can be inhibited by antibodies, SSIII activity was measured by unit assay in the presence and absence of mouse anti-SSIII monoclonal antibodies (mAb). Anti-SSIII clones #2 and #4 did not directly inhibit SSIII activity, either alone or in combination, even to 10 fold molar excess of mAb to SSIII (FIG. 1). However, the addition of goat-anti-mouse-IgG-horse radish peroxidase (anti-IgG-HRP) in combination with anti-SSIIII clones #4 and #2 strongly inhibited SSIII activity (FIG. 1). This inhibition was specific to anti-SSIII mAb components, as SSIII activity was inhibited by anti-IgG-HRP in combination with any of an additional four independent anti-SSIII mAbs, but not with an anti-ThermoScript mAb (DE11) (FIG. 2). Denaturing the anti-SSIII mAbs before adding anti-IgG-HRP prevented the majority of the SSIII inhibition (FIG. 1), as did titrating the amount of anti-IgG-HRP (FIG. 2). Furthermore, anti-IgG-HRP by itself produced little inhibition of SSIII activity (data not shown). Taken together, these results indicate that both components of the inhibitory complex (the SSIII-specific mAb and the inhibitory anti-IgG mAb) must be present for strong inhibition of SSIII activity.

Figure 3:
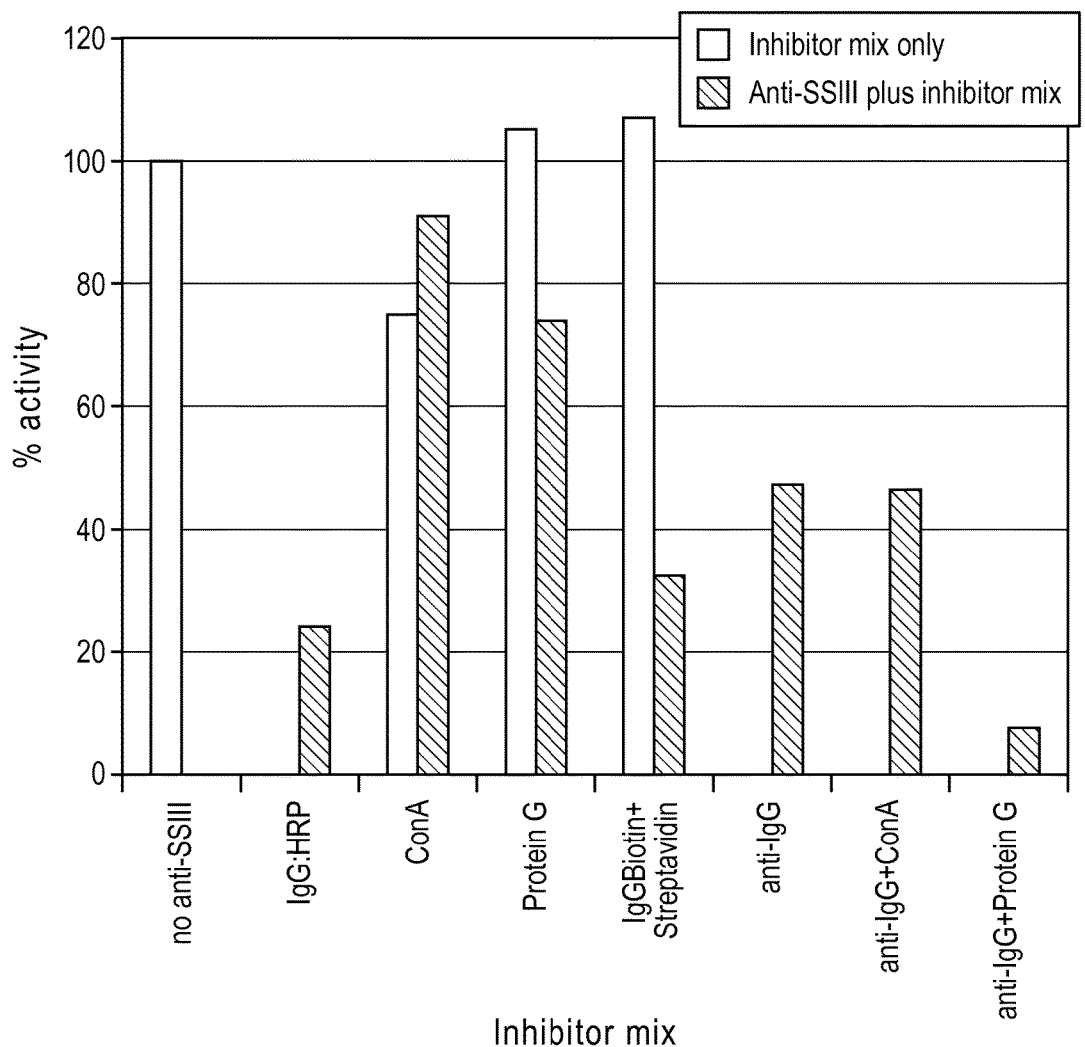
FIG. 3. Bar graph showing the effect of anti-SSIII primary mAb and several different inhibitor components on SSIII activity. SSIII activity is depicted in the presence of each specified inhibitor component either without anti-SSIII primary mAb (light bars), or with anti-SSIII primary mAb (dark bars). SSIII activity in reactions is normalized to that in Column 1. Column 1: No primary mAb or inhibitor components. Column 2: Goat-anti-mouse-IgG-Horse radish peroxidase. Columns 3-4: Concavalin A (ConA). Columns 5-6: Protein G-AlexaFluor 488. Columns 7-8: Goat-anti-mouse-IgG-biotin+Streptavidin. Column 9: Goat anti-mouse-IgG. Column 10: Goat anti-mouse-IgG+ConA. Column 11: Goat anti-mouse-IgG+Protein G-AlexaFluor 488.

To determine if components other than anti-IgG-HRP could effectively inhibit SSIII activity in conjunction with anti-SSIII, a variety of molecules that interact with antibodies were screened for the ability to inhibit SSIII in the presence and absence of anti-SSIII. The lectin Concavalin A, AlexaFluor 488 conjugated streptococcal antibody-binding protein G, anti-IgG, and the anti-IgG-biotin+streptavidin complex all produced little or no inhibition of SSIII activity by themselves (FIG. 3, and data not shown for anti-IgG). However, in conjunction with anti-SSIII, protein G-AlexaFluor 488, anti-IgG, and anti-IgG-biotin+streptavidin each partially inhibited SSIII, while anti-IgG+Protein G-AlexaFluor 488 very strongly inhibited SSIII (FIG. 3). These results indicate that a variety of antibody-interacting molecules can couple with the anti-SSIII to effect SSIII inhibition.

Figure 4:
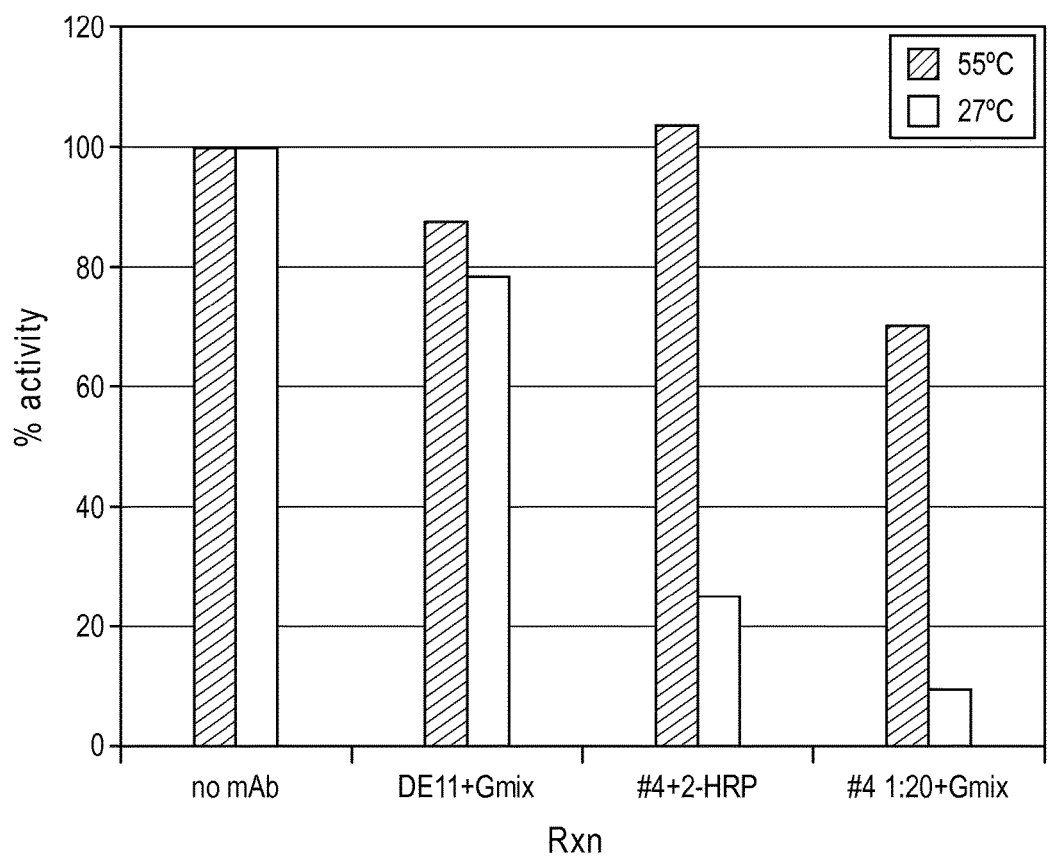
FIG. 4. Bar graph showing the effect of multicomponent inhibitors at different temperatures on SSIII activity. Light bars depict polymerase activity at 27° and dark bars depict activity at 55°. SSIII polymerase activity in each reaction is normalized to that in Column 1. Columns 1-2: No primary mAb or inhibitor components. SSIII activity at 27° and 55° are each independently set to 100% by definition. Columns 3-4: Anti-ThermoScript primary mAb with Gmix (Goat-anti-mouse-IgG+Protein G-Alexafluor 488). Columns 5-6: Anti-SSIII primary mAb with goat-anti-mouse-IgG-horse radish peroxidase. Columns 7-8: Anti-SSIII primary mAb with Gmix.

To determine if inhibition of SSIII by the multi-component complex is reversible, SSIII unit-activity was measured at both room temperature and at a temperature where the antibody should be destabilized/denatured(55°). In agreement with previous experiments, SSIII was strongly inhibited by both anti-IgG-HRP and anti-IgG+Protein G-AlexaFluor 488 (Gmix) at room temperature in the presence of anti-SSIII but not anti-ThermoScript (DE11) (FIG. 4). As expected, the SSIII inhibition seen at room temperature was strongly reversed at 55°. These data demonstrate that these SSIII-inhibitor formulations have the potential to be useful, reversible, inhibitors of RT activity at room temperature.

Figure 5:
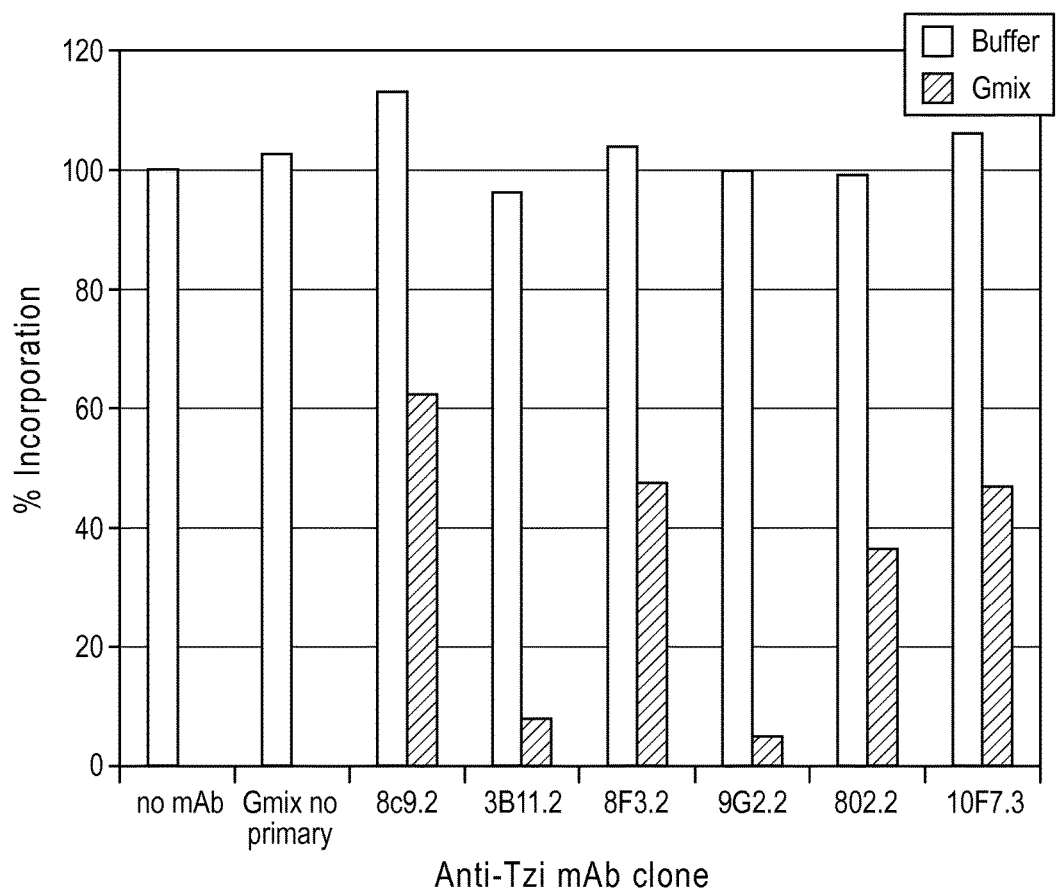
FIG. 5. Bar graph showing the effect of multicomponent inhibitors on *Thermococcus zilligi* (Tzi) thermostable DNA polymerase activity. Tzi activity is depicted in the presence of each specified component with the addition of buffer only (light bars) or Gmix (goat anti-mouse-IgG+Protein G-AlexaFluor 488, dark bars). Tzi polymerase activity in each reaction is normalized to that in Column 1. Column 1: No primary anti-Tzi antibody or inhibitor components. Set to 100% by definition. Column 2: Gmix only. Columns 3-4: Primary anti-Tzi antibody clone 8C9.2. Columns 5-6: Primary anti-Tzi antibody clone 3B11.2. Columns 7-8: Primary anti-Tzi antibody clone 8F3.2. Columns 9-10: Primary anti-Tzi antibody clone 9G2.2. Columns 11-12: Primary anti-Tzi antibody clone 802.2. Columns 13-14: Primary anti-Tzi antibody clone 10F7.3.
Figure 6:
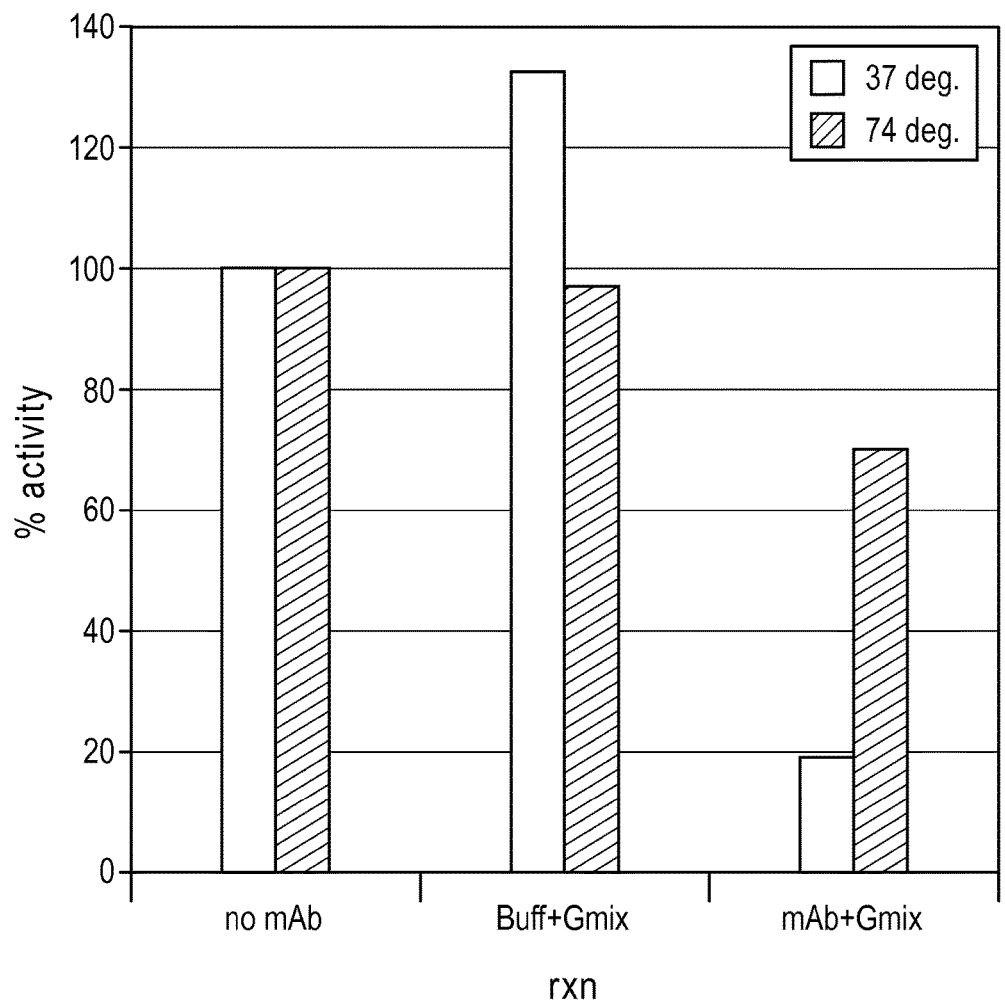
FIG. 6. Bar graph showing the effect of multicomponent inhibitors at different temperatures on Tzi activity. Light bars depict Tzi activity at 37° C. and dark bars depict activity at 74° C. Tzi polymerase activity in reactions is normalized to that in Column 1. Columns 1-2: No primary anti-Tzi mAb or inhibitor components. Tzi activity at 37° and 74° are each independently set to 100% by definition. Columns 3-4: Gmix (goat-anti-mouse-IgG+Protein G-AlexaFluor 488) without primary anti-Tzi mAb. Columns 5-6: Primary anti-Tzi mAb clone 1G11.3 with Gmix.

Inhibition of Tzi, RT41A and Taq Polymerase Activity by Multicomponent Inhibitors To determine if the principle of multi-component inhibitors can be applied to enzymes other than SSIII, inhibition of the thermostable DNA polymerases Tzi, RT41A, and Taq was assayed in the presence and absence of multi-component inhibitors. Each of six primary mouse anti-Tzi mAbs failed to directly inhibit Tzi by themselves, as did Gmix by itself (FIG. 5). However, in combination with Gmix, each of the six anti-Tzi mAbs produced moderate to strong inhibition of Tzi (FIG. 5). Furthermore, as seen with SSIII multicomponent inhibitors, the inhibition of Tzi at lower temperatures was significantly reversed at elevated temperatures (FIG. 6). Multi-component inhibitors have thus been demonstrated to be effective and reversible inhibitors of reverse transcriptases and DNA polymerase, and are likely to be broadly applicable inhibitors of many classes of enzymes.

Figure 7:
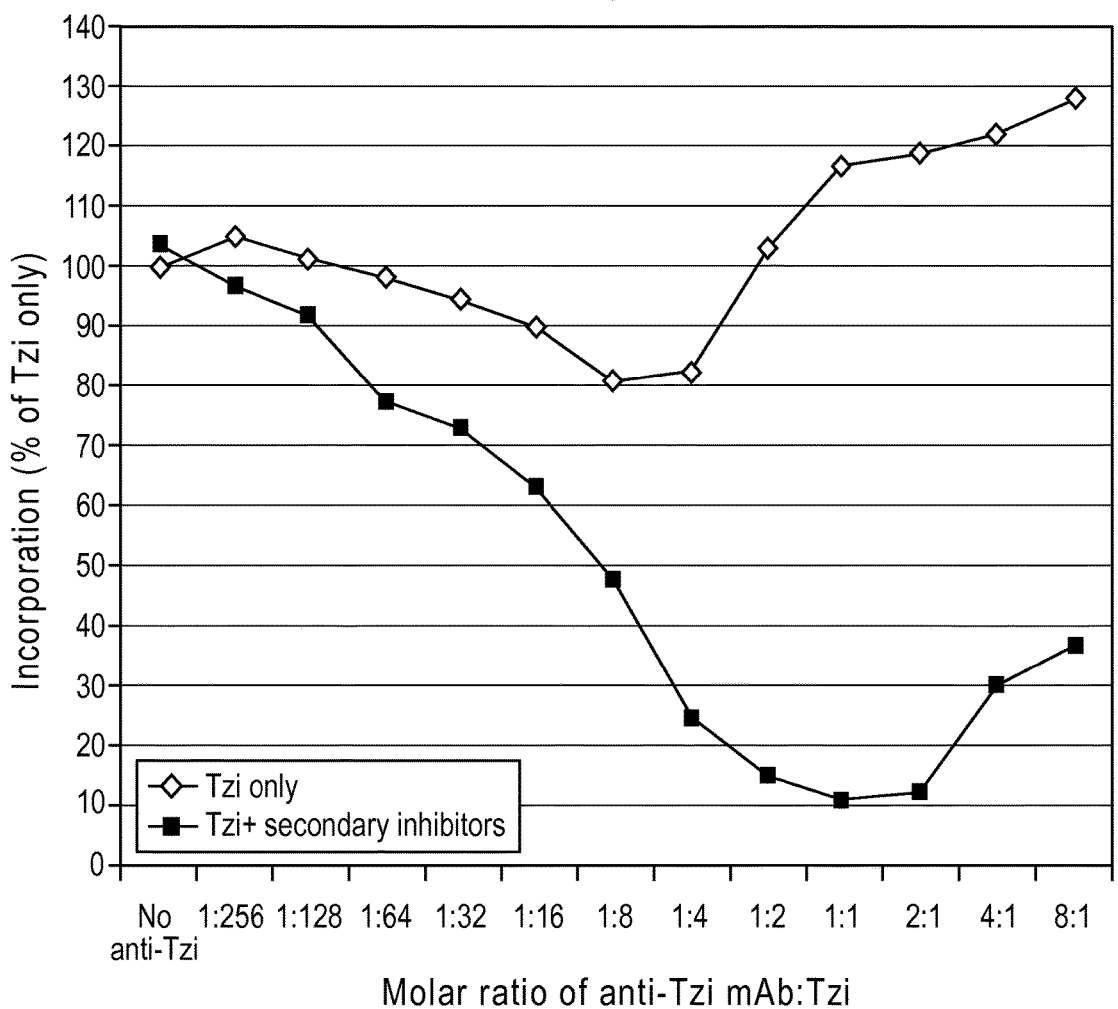
FIG. 7. Line graph showing Tzi polymerase activity in the presence of increasing concentrations of anti-Tzi polymerase monoclonal antibodies in the presence of absence of secondary inhibitors.
Figure 8:
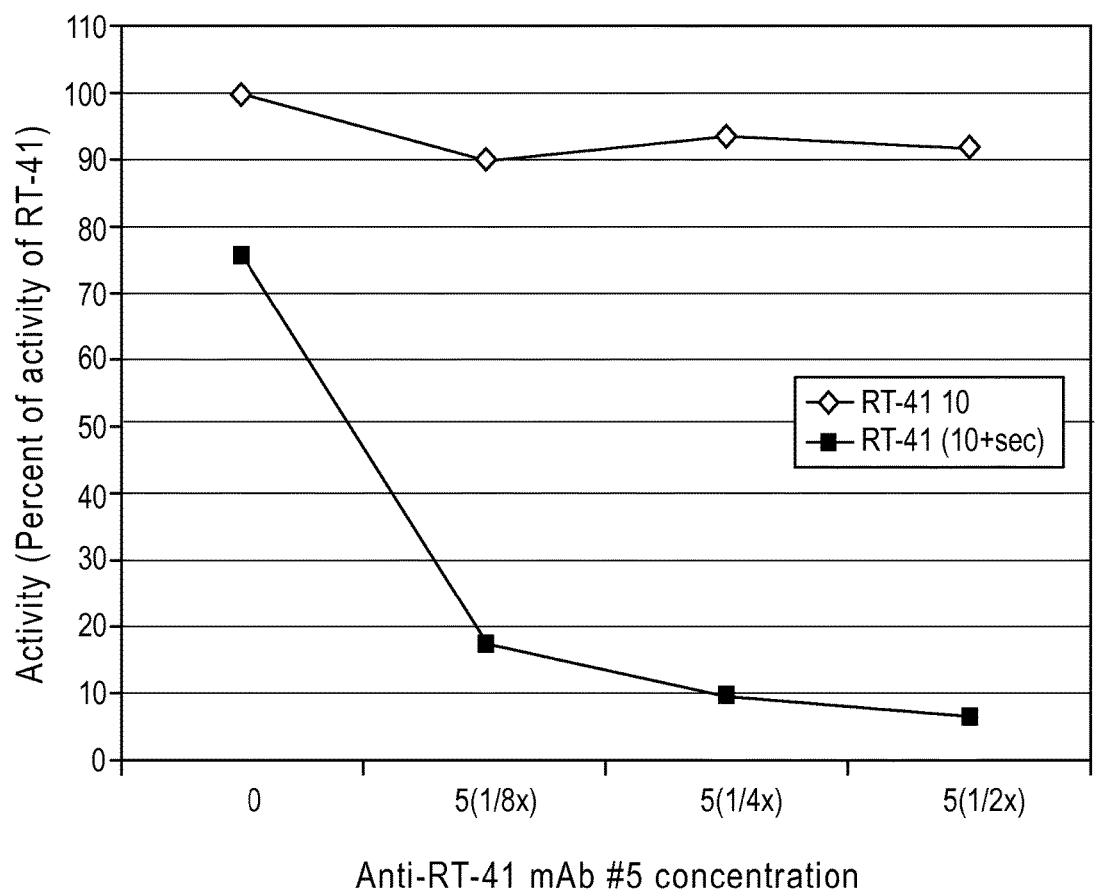
FIG. 8. Line graph showing RT41A polymerase activity in the presence of constant concentration of anti-RT41A mAb #10 and increasing concentrations of anti-RT41A mAb #5 with or without rabbit anti-mouse IgG secondary antibody.
Figure 9:
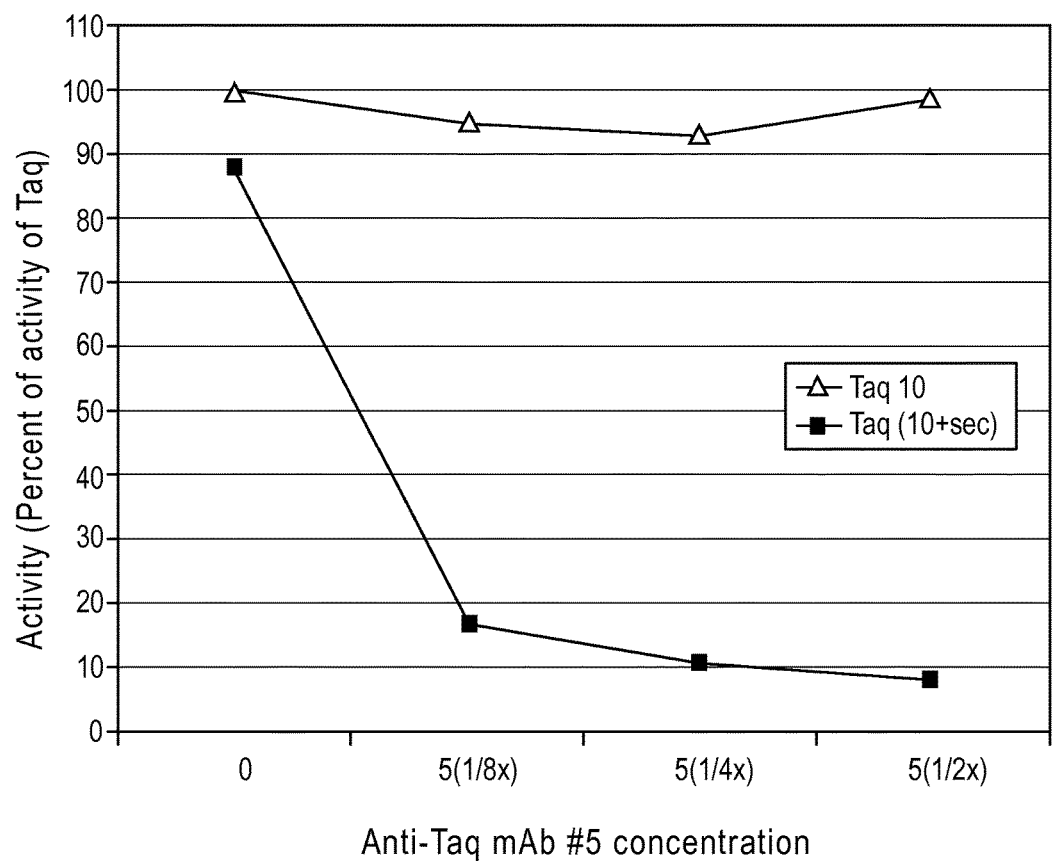
FIG. 9. Line graph showing Taq polymerase activity in the presence of constant concentration of anti-Taq mAb #10 and increasing concentrations of anti-Taq mAb #5 with or without rabbit anti-mouse IgG secondary antibody.

To determine the effect of the molar ratio of anti-Tzi monoclonal antibody on Tzi polymerase activity, the Tzi unit assay was performed with no anti-Tzi monoclonal antibody, or in the presence of increasing molar ratios of anti-Tzi to Tzi (between 1:256 and 8:1). Tzi unit activity was measured at 37 C in the presence of increasing concentrations of anti-Tzi mAbs 9G3.3+6F3.2, either with or without a secondary inhibitor mixture comprising a 4:1 molar ratio rabbit-anti-mouse IgG:Tzi and 4:1 molar ratio protein G:Tzi. At a 1:1 molar ratio of anti-Tzi mAbs:Tzi, in the absence of secondary inhibitors, Tzi activity was potentiated, whereas in the presence of secondary inhibitors, Tzi activity was maximally inhibited (FIG. 7). Tzi inhibition began to be lost above molar ratios of anti-Tzi mAB:Tzi of 2:1, most likely due to titration of the secondary inhibitors by the excess of Tzi. Similar results to the above were also obtained with RT41A (FIG. 8) and Taq (FIG. 9) DNA polymerases using anti-RT41A and anti-Taq monoclonal antibodies with rabbit-anti-mouse-IgG secondary antibody.

Figure 10:
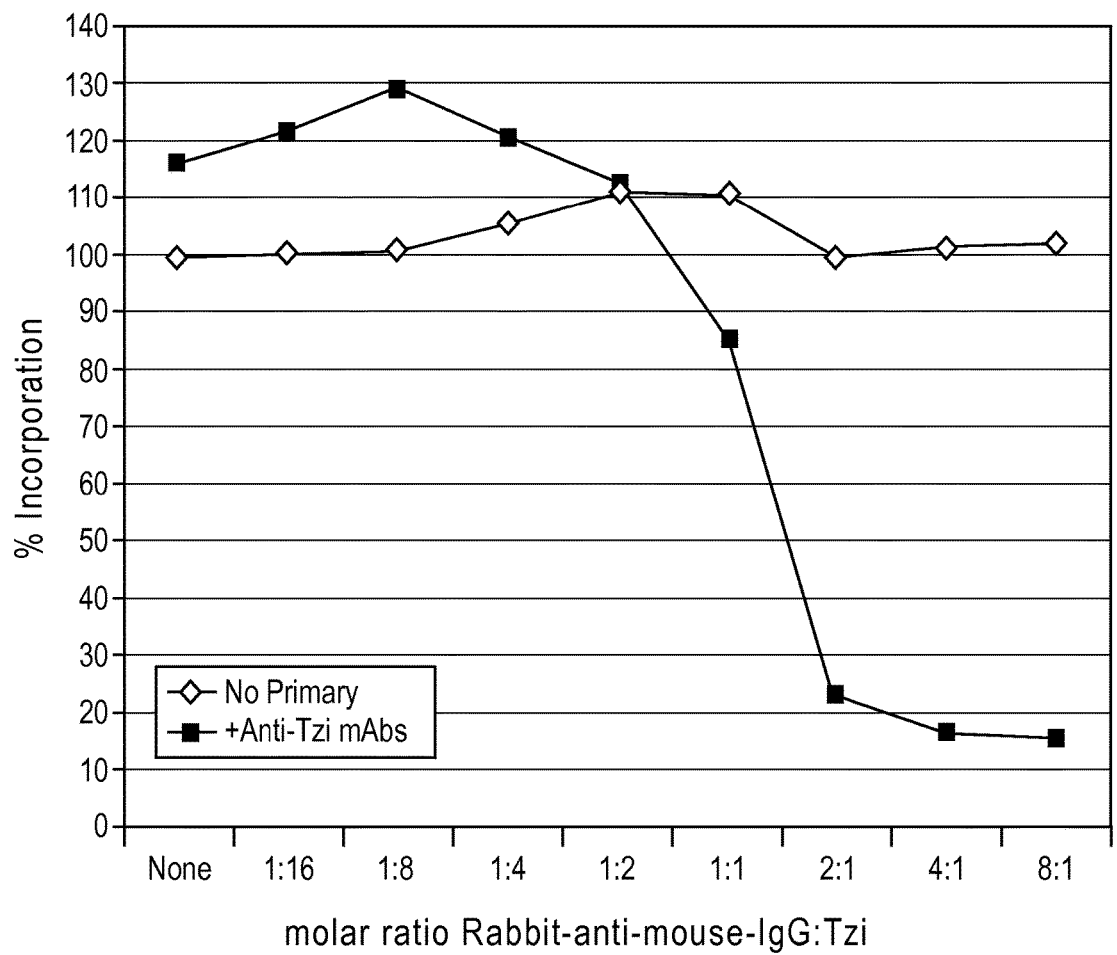
FIG. 10. Line graph showing Tzi polymerase activity in the presence of increasing concentrations of rabbit-anti-mouse IgG in the presence or absence of anti-Tzi polymerase monoclonal antibodies.

To determine the effect of the molar ratio of rabbit-anti-mouse-IgG on Tzi polymerase activity, the Tzi unit assay was performed in the presence of increasing concentrations of rabbit-anti-mouse-IgG (between 1:16 and 8:1) either with or without a 1:1 molar ratio of anti-Tzi mAbs (9G3.3+6F3.2):Tzi. Molar ratios of rabbit-anti-mouse-IgG:Tzi as low as 4:1 maximally inhibited Tzi activity in the presence but not the absence of anti-Tzi mAbs (FIG. 10).

Figure 11:
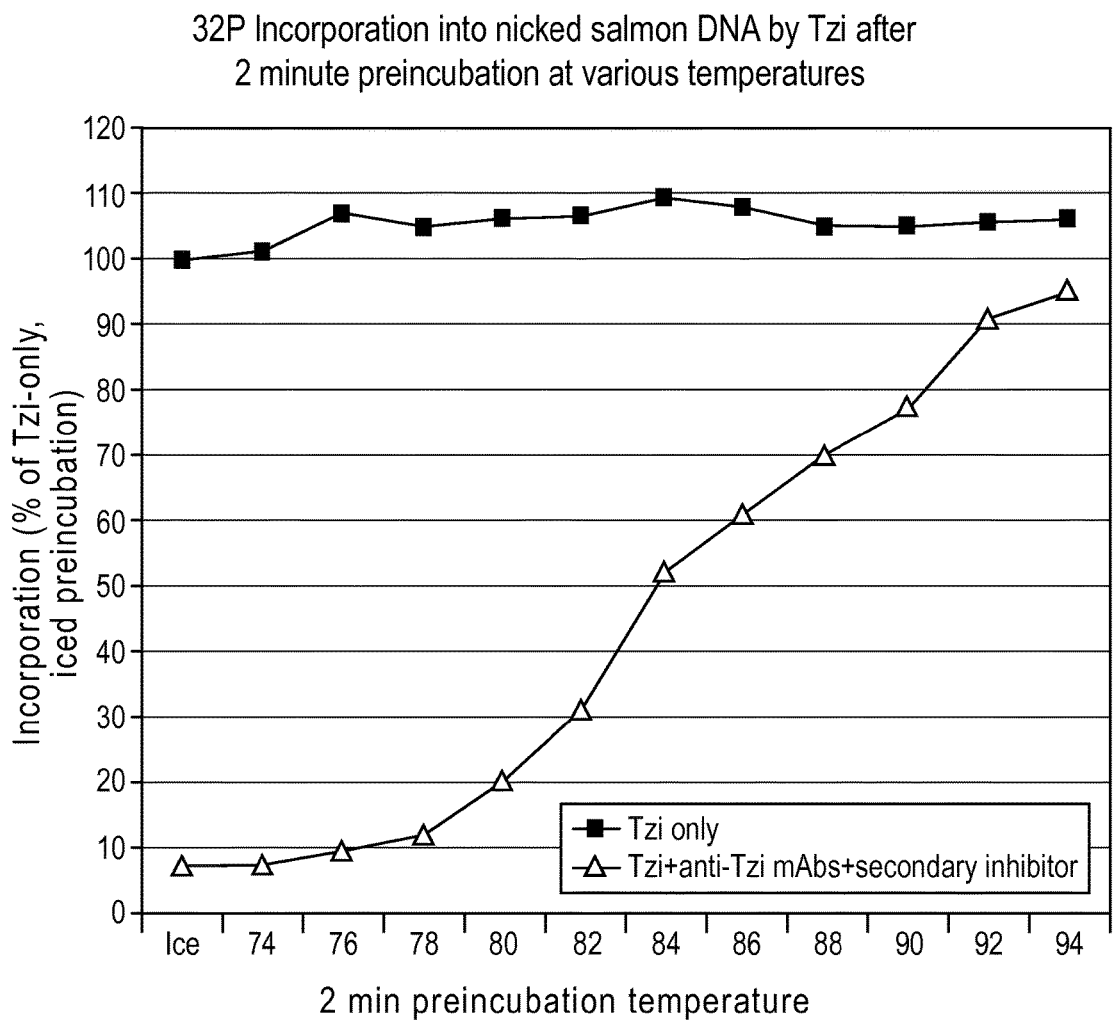
FIG. 11. Line graph showing Tzi polymerase activity after 2 minutes of preincubation at various temperatures in the presence of absence of anti-Tzi polymerase monoclonal antibody and secondary inhibitors.

To determine the effect of preincubation temperature on Tzi activity, Tzi alone or (Tzi+anti-Tzi mAbs+rabbit-anti-mouse IgG) was preincubated at various temperatures for 2 minutes prior to performing the Tzi unit assay. Tzi activity was measured at 37° C. after the preincubation, and nearly full activity was regained after as little as 2 minutes preincubation at 94° C. (FIG. 11).

Figure 12:
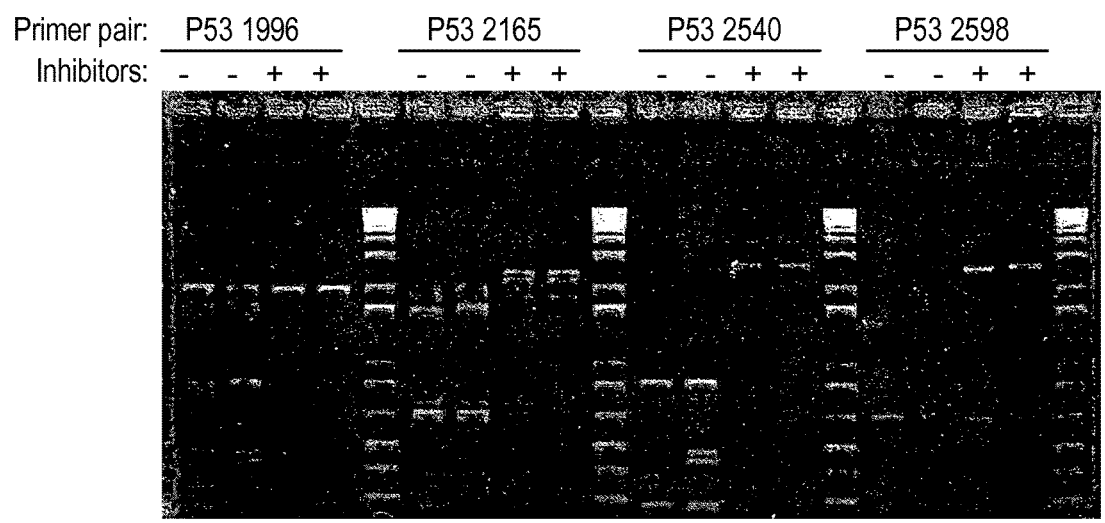
FIG. 12. Gel showing, in duplicate, PCR products obtained using Tzi polymerase to amplify four different amplicons from genomic DNA, either in the absence (−) or presence (+) of 2 monoclonal mouse anti-Tzi antibodies and a monoclonal rat anti-mouse secondary antibody. The desired PCR product is the uppermost band in the (+) lanes.

Multi-component polymerase inhibitors can improve PCR specificity and yield, as shown with Tzi in FIG. 12 (the desired PCR product is the uppermost band in each lane).

Figure 13:
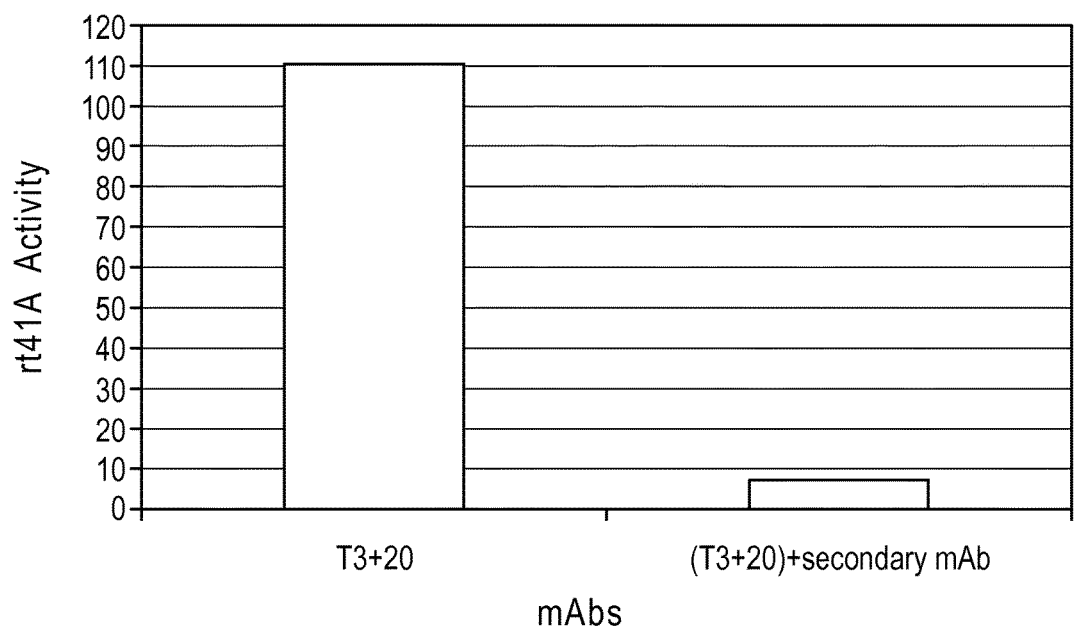
FIG. 13. Bar graph showing inhibition of RT41A by 2 monoclonal mouse anti-RT41A antibodies ("T3" and "20") and a monoclonal rat anti-mouse secondary antibody.

FIG. 13 shows that RT41A activity is not substantially inhibited by 2 monoclonal mouse anti-RT41A antibodies (i.e., PBAs) alone, but that these antibodies together with a monoclonal rat anti-mouse secondary antibody (i.e., PBA binding molecule) inhibit RT41A activity more than 90%.

Figure 14:
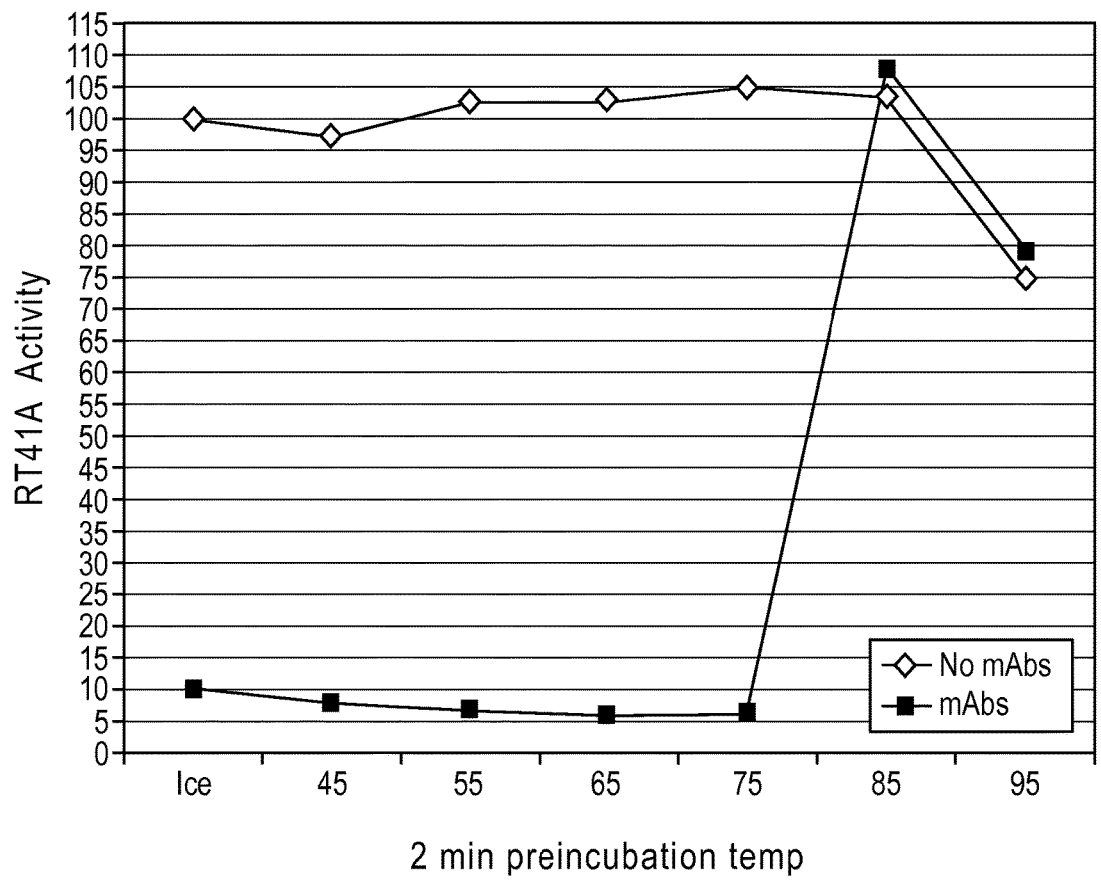
FIG. 14. Line graph showing polymerase activity after 2 minutes preincubation at various temperatures in the presence of absence of 2 monoclonal mouse anti-RT41A antibodies and a monoclonal rat anti-mouse secondary antibody.

FIG. 14 shows reversible inhibition of RT41A by a multi-component inhibitor consisting of 2 monoclonal mouse anti-RT41A antibodies (i.e., PBAs) and a monoclonal rat anti-mouse secondary antibody (i.e., PBA binding molecule). This multi-component inhibitor inhibits RT41A activity at least 90% at temperatures lower than about 85° C., and inhibition by this multi-component inhibitor is relieved at temperatures greater than about 85° C.

What is claimed is:

1. A composition comprising:
   (a) a thermostable DNA polymerase, wherein said thermostable DNA polymerase is selected from the group consisting of: *Thermus aquaticus* (Taq) DNA polymerase, *Thermus filiformis* (Tfi) DNA polymerase, and *Thermococcus zilligi* (Tzi) DNA polymerase; and
   (b) a primary monoclonal antibody that binds to said polymerase, and
   (c) a secondary anti-IgG polyclonal antibody that binds to said primary antibody,
   wherein said primary antibody alone, when bound to said polymerase, inhibits polymerase activity by 10% or less,
   and wherein said primary antibody in complex with said secondary antibody, when bound to said polymerase, inhibits polymerase activity by 90% or more.

2. The composition of claim 1, wherein said inhibition of said polymerase by said primary antibody with said secondary antibody is reversible.

3. The composition of claim 2, wherein said inhibition of said polymerase by said primary antibody with said secondary antibody is reversible by heating to a temperature of at least 40° C.

4. The composition of claim 1, wherein said primary and/or said secondary antibody is a derivatized antibody.

5. The composition of claim 1, wherein said primary antibody and/or said secondary antibody is detectably labeled.

6. The composition of claim 5, wherein said primary antibody and/or said secondary antibody is detectably labeled with horseradish peroxidase (HRP), rhodamine, biotin, fluorescein, alkaline phosphatase, or AlexaFluor488.

7. The composition of claim 1, wherein said composition further comprises one or more nucleoside triphosphates and/or deoxynucleoside triphosphates.

8. The composition of claim 1, wherein said Taq, Tfi or Tzi DNA polymerase is recombinant.

9. The composition of claim 1, wherein said secondary antibody is coupled with a protein or polymer.

10. The composition of claim 9, wherein said protein is horseradish peroxidase, alkaline phosphatase, or albumin.

11. The composition of claim 9, wherein said polymer is a polyethylene glycol, a polyoxyethylene, a polyoxypropylene, or a polyoxyethylene/polyoxypropylene copolymer.

\* \* \* \* \*